US005614638A

United States Patent [19]
Ranganathan et al.

[11] Patent Number: 5,614,638
[45] Date of Patent: Mar. 25, 1997

[54] NONIONIC RADIOGRAPHIC CONTRAST AGENTS

[75] Inventors: Ramachandran S. Ranganathan, Princeton; Thangavel Arunchalam, Plainsboro; Edmund R. Marinelli, Lawrenceville; Radhakrishna K. Pillai, Kendall Park, all of N.J.

[73] Assignee: Bracco International B.V., Amsterdam, Netherlands

[21] Appl. No.: 894,691

[22] Filed: Jun. 5, 1992

Related U.S. Application Data

[63] Continuation-in-part of Ser. No. 710,884, Jun. 6, 1991, abandoned, which is a continuation-in-part of Ser. No. 617,716, Nov. 26, 1990, abandoned, which is a continuation-in-part of Ser. No. 442,869, Nov. 29, 1989, abandoned.

[51] Int. Cl.$^6$ .................................. C07D 207/02
[52] U.S. Cl. ..................... 548/543; 548/544; 548/545; 548/547; 548/551
[58] Field of Search .................... 548/543, 544, 545, 547, 551

[56] References Cited

U.S. PATENT DOCUMENTS

| 2,750,393 | 6/1956 | Elpern | 548/543 |
| 2,776,241 | 1/1957 | Priewe et al. | 548/543 |
| 3,306,927 | 2/1967 | Larsen | 548/543 |

(List continued on next page.)

FOREIGN PATENT DOCUMENTS

| 0022744 | 5/1989 | European Pat. Off. . |
| 0390242 | 2/1990 | European Pat. Off. . |
| 0082803 | 2/1990 | European Pat. Off. . |
| 0026281 | 2/1991 | European Pat. Off. . |
| 2007674 | 2/1990 | France . |
| 3429949 | 3/1980 | Germany . |
| 0105752 | 4/1988 | Germany . |
| 2726196 | 4/1990 | Germany . |
| 319226 | 3/1990 | Norway . |
| WO9109007 | 6/1990 | WIPO . |

OTHER PUBLICATIONS

Fumagalli, et al., "Radiopaque Contrast Media", *Pharmazie*, 30, H.2, pp. 78–79. (1980).
Stormorken et al., "Effect of Various Contrast Media on Coagulation, Fibrinolysis, and Platelet Function: An In Vitro and In Vivo Study", *Investigative Radiology*, vol. 21, Apr. 1986, pp. 348–354.
Mamon et al., "Biochemical Evidence for a Relative Lack of Inhibition of Thrombin Formation by Nonionic Contrast Media", *Radiology* 1991; 179:399–401.
G. B. Hoey et al., "Chemistry of X–Ray Contrast Media" pp. 23–125. (1989).
Laerum et al., "Postphlebographic Thrombosis", *Diagnostic Radiology*, Sep. 1981, pp. 651–654.

*Primary Examiner*—Johann Richter
*Assistant Examiner*—John Peabody
*Attorney, Agent, or Firm*—George P. Hoare; Donald L. Rhoads

[57] ABSTRACT

New nonionic radiographic contrast agents having the formula

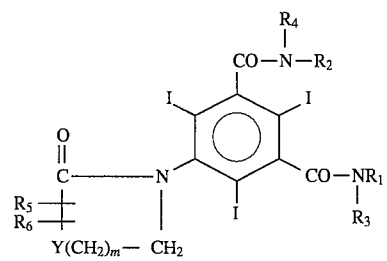

wherein Y is a single bond, $-CH_2CH_2-$, $-CH_2O-$, $-OCH_2-$,

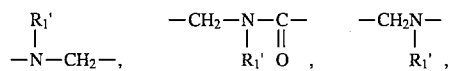

$-CH_2-$, $-CH_2-CH_2-CH_2-$, $-O-$ or

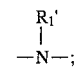

$R_1$, $R_1'$ and $R_2$ are the same or different and are hydrogen, alkyl or hydroxyalkyl.

Hydroxyalkyl refers to such alkyl groups having 1 or more hydroxy groups. Preferred hydroxyalkyl groups include:

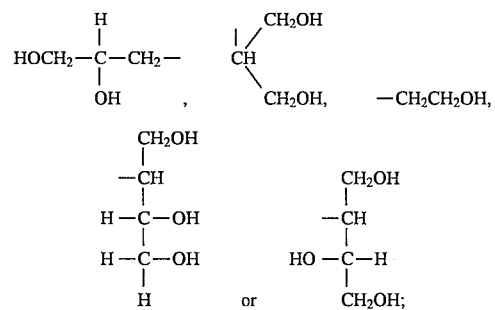

$R_3$ and $R_4$ are the same or different and are hydrogen, methyl or $-CH_2CH_2OH$; $R_5$ is hydrogen, alkyl, $-CH_2CH_2OH$, $CH_2OH$ or OH and $R_6$ is alkyl, $-CH_2CH_2OH$, $CH_2OH$, OH or hydrogen and may be the same or different than $R_5$ and m is zero or one, with the proviso that no methylene or methine carbon atom of the heterocyclic ring is attached to both a nitrogen and an oxygen atom with the additional proviso that when Y is a single bond, m is not zero.

These new contrast agents are water soluble and have desirable low osmolality and anticoagulant properties.

6 Claims, No Drawings

U.S. PATENT DOCUMENTS

| | | | |
|---|---|---|---|
| 3,701,771 | 10/1972 | Almen et al. | 548/543 |
| 3,883,535 | 5/1975 | Felder et al. | 548/543 |
| 3,890,318 | 6/1975 | Obendorf et al. | 548/543 |
| 3,925,412 | 12/1975 | Obendorf et al. | 548/543 |
| 4,001,298 | 1/1977 | Gries et al. | 548/543 |
| 4,001,323 | 1/1977 | Felder et al. | 548/543 |
| 4,066,743 | 1/1978 | Kneller | 548/543 |
| 4,250,113 | 2/1981 | Nordal et al. | 548/543 |
| 4,352,788 | 10/1982 | Felder et al. | 548/543 |
| 4,845,235 | 7/1989 | Matumoto et al. | 548/543 |
| 4,962,204 | 10/1990 | Wambach | 548/543 |

NONIONIC RADIOGRAPHIC CONTRAST AGENTS

This application is a continuation-in-part of U.S. Ser. No. 710,884 filed Jun. 6, 1991, now abandoned, which is a continuation-in-part of U.S. Ser. No. 617,716, filed Nov. 26, 1990, now abandoned, which is a continuation-in-part of U.S. Ser. No. 442,869, filed Nov. 29, 1989, now abandoned.

BACKGROUND OF THE INVENTION

This invention relates to new nonionic radiographic contrast agents having desirable water solubility and low osmolality properties. These new compounds are derivatives of the 5-amino-2,4,6-triiodo-1,3, benzenecarboxylic acid moiety, wherein the 5 amino nitrogen atom is part of a 4, 5, 6 or 7-membered heterocyclic ring.

DESCRIPTION OF THE PRIOR ART

Ionic contrast agents that contain a heterocyclic ring and an iodobenzene moiety have been reported in the literature. For instance Iodophthalein is disclosed in Amer. J. Pharm., 100, 374 (1928). U.S. Pat. No. 2,776,241 discloses dimeric compounds with heterocyclic bridges. U.S. Pat. No. 3,306,927 discloses heterocycles as counter ions. U.S. Pat. No. 2,750,393 discloses ionic cholecystopaques. British Patent 1,191,015 discloses 3,5-diaminobenzoic acids. U.S. Pat. No. 4,066,743 discloses 5-aminoisophthalic acids. U.S. Pat. No. 4,250,113 discloses 3-aminobenzoic acids.

Non-ionic contrast agents having a heterocyclic ring including sugar ethers, acyl amides or aminosugars and reversed amides from keto-sugars have been disclosed in the prior art.

SUMMARY OF THE INVENTION

The new radiographic contrast agents of this invention have the formula

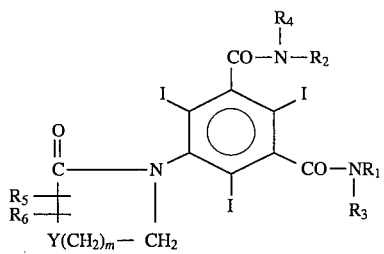

wherein Y is a single bond, —$CH_2CH_2$—, —$CH_2O$—, —$OCH_2$—,

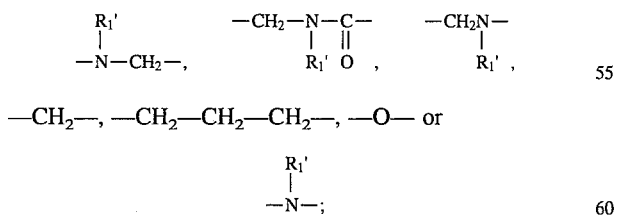

—$CH_2$—, —$CH_2$—$CH_2$—$CH_2$—, —O— or

—N—;
|
$R_1'$ $R_1$, $R_1'$ and $R_2$ are the same or different and are hydrogen, alkyl or hydroxyalkyl;

$R_3$ and $R_4$ are the same or different and are hydrogen, alkyl or —$CH_2CH_2OH$; $R_5$ is hydrogen, alkyl, —$CH_2CH_2OH$, $CH_2OH$ or OH and $R_6$ is alkyl, —$CH_2CH_2OH$, $CH_2OH$, OH or hydrogen and may be the same or different than $R_5$ and m is zero or one, with the proviso that no methylene or methine carbon atom of the heterocyclic ring is attached to both a nitrogen and an oxygen atom with the additional proviso that when Y is a single bond, m is not zero. The term alkyl refers to straight or branched chain groups of one to six carbon atoms including methyl, ethyl and propyl.

Hydroxyalkyl refers to such alkyl groups having one or more hydroxy moieties. Preferred hydroxyalkyl groups include

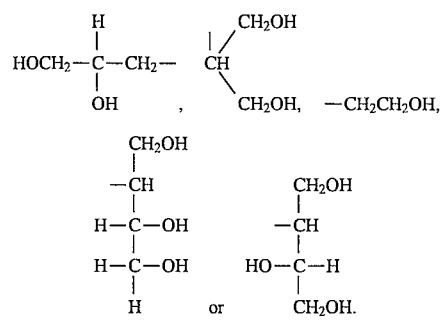

DESCRIPTION OF THE PREFERRED EMBODIMENTS

The compounds of formula I all have a molecular weight of from 780 to 835. They have from four to six hydroxy groups per monomeric unit. They all have one or two tertiary nitrogen atoms. Compounds with one tertiary atom are preferred. This unique set of parameters allows for new non-ionic contrast agents which exhibit low toxicity, high chemical stability, ease of chemical synthesis, low viscosity and low osmolality of concentrated aqueous solutions of the contrast agent.

The following groups substituted and unsubstituted are representative of the heterocycles connected to the 5-position of the benzene ring in Formula I:

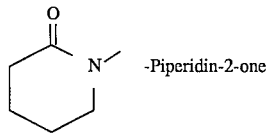
A -Piperidin-2-one

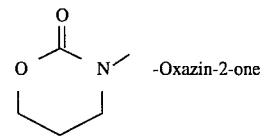
B -Oxazin-2-one

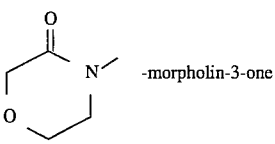
C -morpholin-3-one

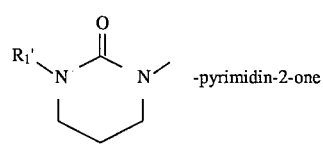
D -pyrimidin-2-one

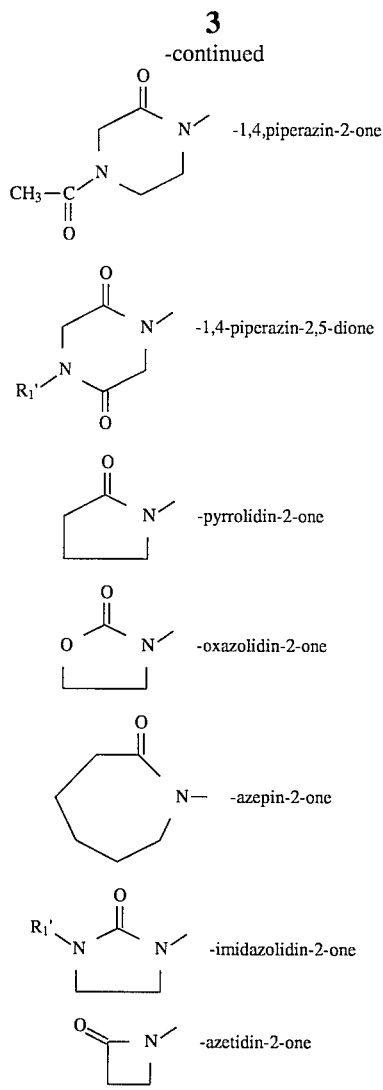

It is noted that when Y is

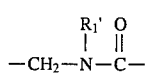

it includes heterocycles represented by formulae E and F. The pyrrolidin-2-one, morpholin-3-one, piperidin-2-one and oxazolidin-2-one are preferred. More preferred is hydroxy and hydroxymethyl substitution on the pyrrolidin-2-one ring. Most preferred is the compound disclosed in Example 8.

The preparation of compounds of formula I wherein the heterocyclic group is oxazolidinyl with 4-hydroxymethyl substitution is illustrated by the following scheme:

Scheme A

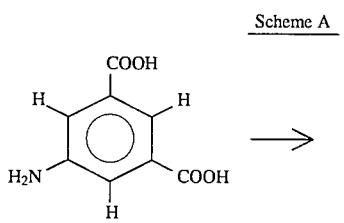

IA

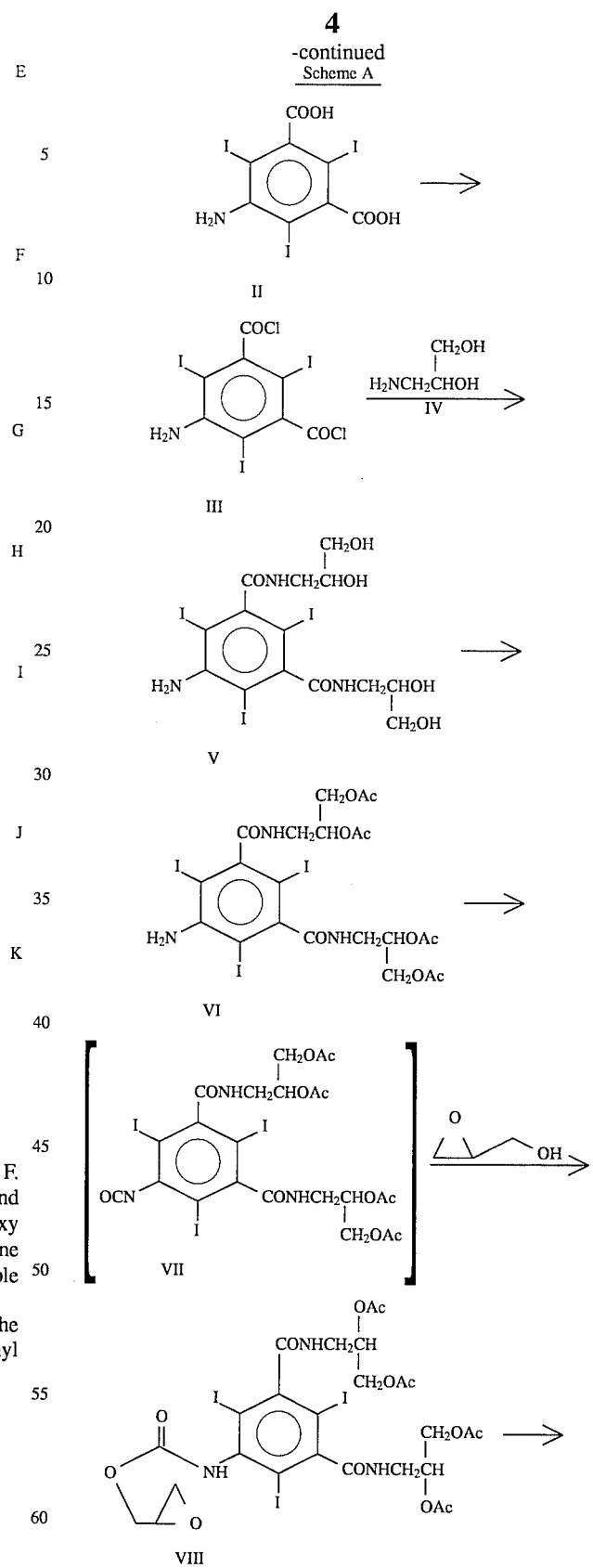

-continued
Scheme A

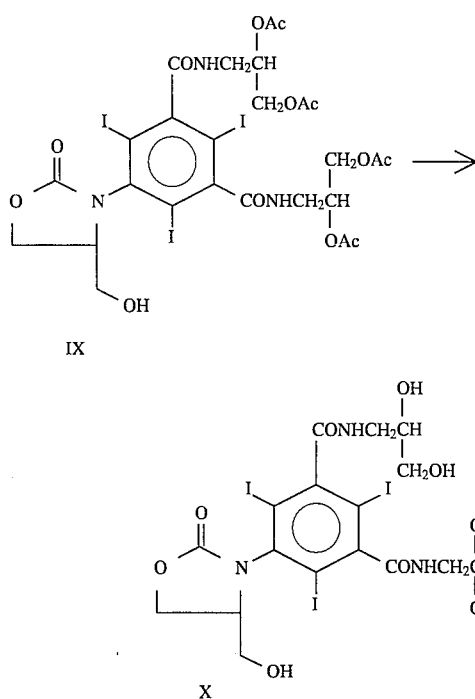

Compound IA which is commercially available is iodinated with a compound such as potassium iododichloride in dilute hydrochloric acid solution to obtain 5-amino-2,4,6,-triiodo-1,3-benzenedicarboxylic acid (II). Compound II is chlorinated with purified thionyl chloride to obtain the corresponding bis-chloride (III). Compound III is then amidated with 1-amino-2,3-propanediol (IV) to obtain the isophthalamide V. Compound V is then selectively O-acylated with acetic anhydride in pyridine to yield 5-amino-N,N'-bis[2,3-bis(acetyloxy)propyl]2,4,6- triiodo-1,3-benzenedicarboxamide (VI). Aminodehalogenation of compound VI by treatment with a toluene solution of phosgene in ethyl acetate at 60° over a period of sixteen hours results in a conversion into the corresponding isocyanate (VII). When the reaction is over, the solvents along with unreacted excess phosgene and hydrogen chloride, that was liberated during the course of the reaction, are removed by distillation. Any trace of acid, left behind, is removed by repeated co-distillations with ethyl acetate.

Addition of glycidol to the crude isocyanate (VII), in the presence of catalysts such as cuprous chloride or phenylmercuric acetate, in ethyl acetate at room temperature overnight yields oxiranylmethyl [3,5-bis[[[2,3-bis(acetyloxy)propyl]amino]carbonyl]2,4,6-triiodophenyl]carbamate (VIII).

A basic solution of the glycidyl carbamate (VIII) is heated at 75° for 30 minutes. Intramolecular cyclization occurs to afford N,N'-bis[2,3bis(acetyloxy)propyl]-5-[4-hydroxymethyl)-2-oxo-3- oxazolidinyl]-2,4,6-triiodo-1,3-benzenedicarboxamide (IX), as the sole product, after crystallization from aqueous methanol.

Deacetylation of the tetraacetate (IX) by treatment with sodium methoxide in methanol, followed by neutralization with Dowex-50-(H⁺) resin and decolorization with charcoal, yields N,N'-bis(2,3-dihydroxypropyl)-5-[4-(hydroxymethyl)-2-oxo-3-oxazolidinyl]-2,4,6-triiodo-1,3-benzenedicarboxamide (X). This product is desalted and further purified by low pressure reverse phase column chromatography.

Crystallization from water or from aqueous isopropanol yields compound X.

The same methodology is employed where $R_1$–$R_4$ are other than above by replacing compound IV with two equivalents of the following compound

when the amide sidechains are to be identical. Similarly, when the amide sidechains are different, III can be reacted with 1.1 equivalent of IVa followed by a second equivalent of IVb

Such two step introduction of two different amine fragments can be accomplished with a bischloride bearing a moiety at C-5 position. For example, in Scheme B a compound of the formula XI is reacted with 1:1 equivalents of XII to provide XIII. Compound XIII is thereafter reacted with ammonia followed by treatment with a base and then an acid toprovide the unsymmetrical amide of Ia.

Scheme B

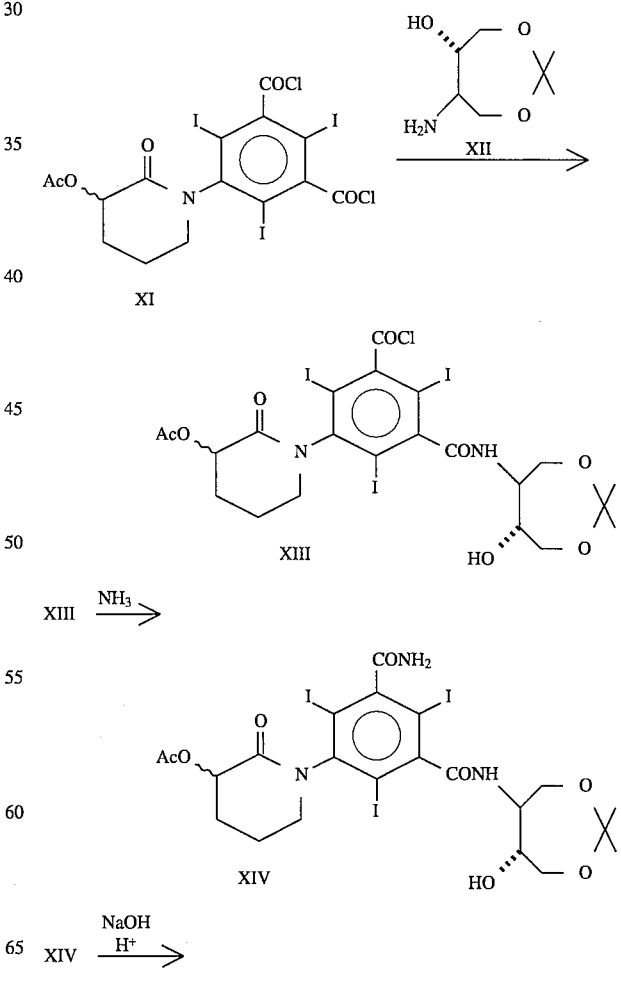

-continued
Scheme B

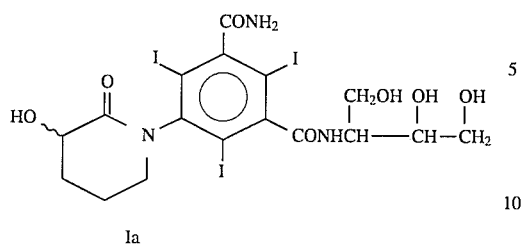

Ia

Substituted pyrrolidin-2-one derivatives with no substitution at the 5 position of the heterocycle are prepared according to Scheme C.

Scheme C

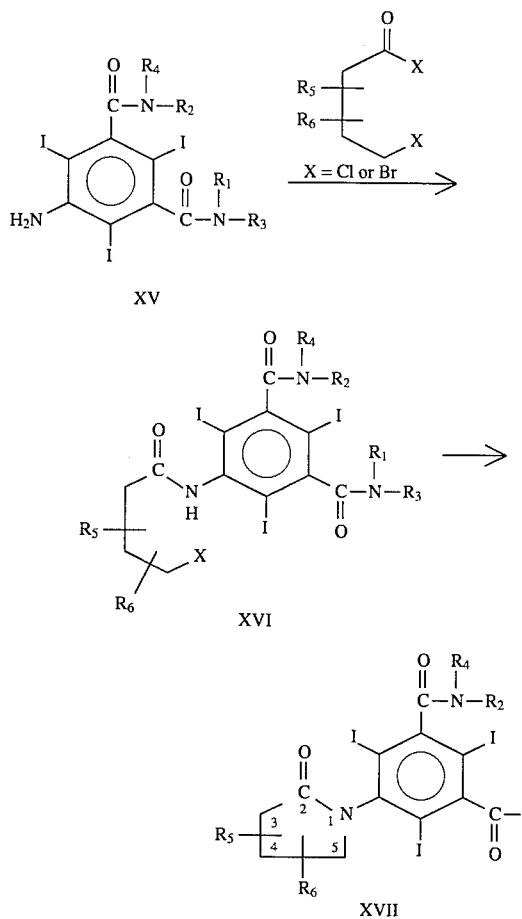

The amide of formula XV is reacted with an ω-halo-acid halide to obtain the anilide of compound XVI followed by cyclization of compound XVI to the pyrrolidine-2-one of formula XVII.

Alternatively, pyrrolidin-2-one derivatives with a hydroxymethyl substitution at the 5-position are prepared by converting the compound of formula XV into the substituted unsaturated anilide having the formula

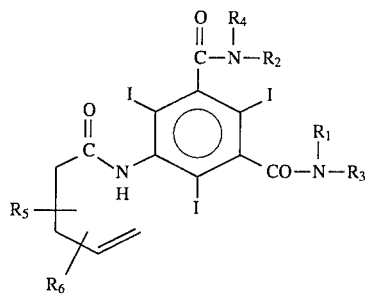

by treatment with a substituted unsaturated acid chloride. Intramolecular cyclization of the compound of formula XVIII through a halonium intermediate, by treatment with an iodinating agent such as N-iodosuccinimide under basic conditions provides the corresponding halomethyl pyrrolidin-2-one having the formula

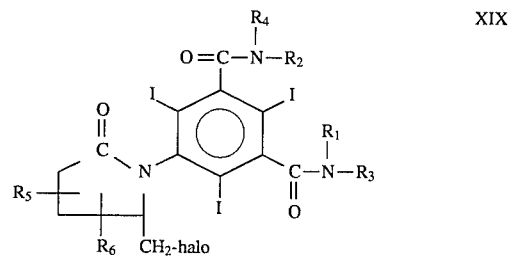

The employment of basic conditions in this cyclization reaction is required to significantly promote N-participative ring closure to afford the pyrrolidine-2-one of formula XIX. In the absence of base, O-cyclization predominates affording unwanted 2-imino-tetrahydrofuran derivatives.

If the substituents $R_1$, $R_2$, $R_3$ and $R_4$ contain acetyloxy groups, they will be deprotected during this ring closure reaction due to the basic conditions employed. The acetyl groups are reintroduced by subjecting the cyclized product to the treatment with acetic anhydride in pyridine.

Compound XIX can be converted into the corresponding hydroxy derivative via the acetyloxy derivative by conventional methods known in the art.

The preparation of compounds of formula I wherein the heterocycle group is azetidin-2-one can be accomplished by treating compound XV with the appropriate substituted unsaturated acid chloride to yield the substituted unsaturated anilide represented below:

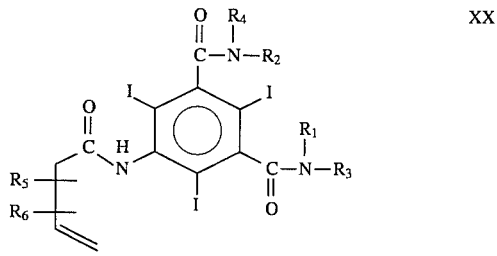

Intramolecular cyclization under basic conditions of compound XX through a halonium intermediate, by treatment with N-iodosuccinimide provides the corresponding halo compound of the formula:

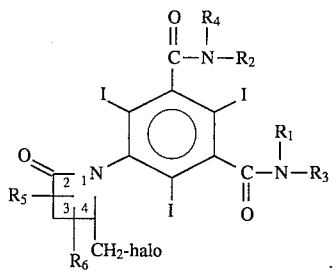
XXI

In this cyclization the possibility exists that 3-halopyrrolidinone could result and this forms yet another synthesis of a halo-substituted pyrrolidinone.

Compound XXI can be converted into the corresponding hydroxy derivative via the corresponding acetyloxy compound using conventional methods known in the art. The unsaturated anilide (XX) can be converted into the corresponding silylimidate represented below

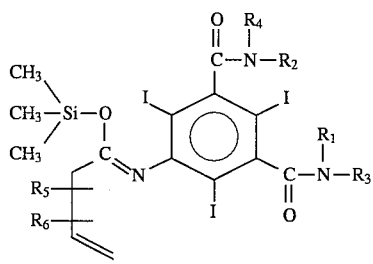
XXII before treatment with iodine or N-iodosuccinimide. Ring closure will then proceed by N-participation as described previously, without competitive O-participation.

The preparation of compounds of formula I wherein the heterocyclic group is azetidin-2-one bearing gem-dialkyl substitution at position 3 of the heterocycle and no substitution at position 4, proceeds best by treating the amine of formula XV with an appropriate acid halide of the formula

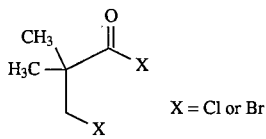
XXIII $X = Cl$ or $Br$ such as,

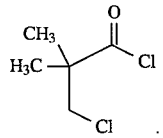
XXIIIa

This provides the anilide of the formula

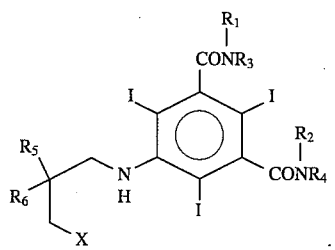
XXIV

Treatment of compound XXIV with a base, e.g., potassium carbonate, in, for example, dimethylacetamide, provides the azetidin-2-one

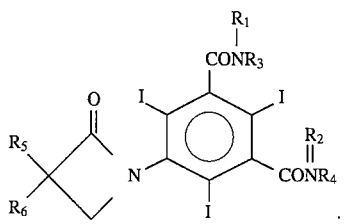
XXV

The compounds of formula I wherein the heterocyclic group is a piperidin-2-one and $R_5$ and $R_6$ are each hydrogen can be prepared by reacting compound XI with an appropriately substituted bromopentanoyl bromide of the formula

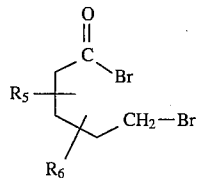
XXVI in a suitable solvent such as dimethylacetamide to yield the corresponding anilide of the formula

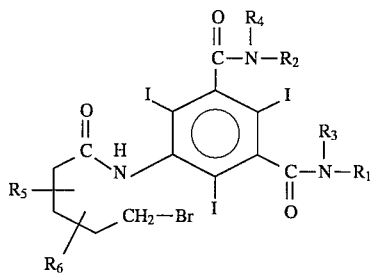
XXVII which upon treatment with a base such as potassium carbonate in a suitable solvent such as dimethylacetamide will yield the desired piperidin-2-one of the formula

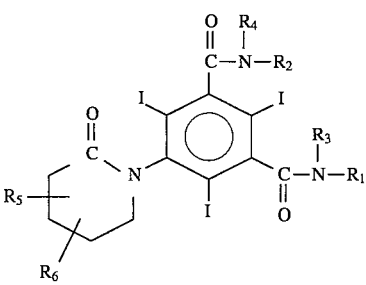
XXVIII

When $R_5$ or $R_6$ is hydroxyl or hydroxymethyl in compound XXVIII it is protected as the corresponding acetate or ether which is eventually deprotected by conventional means. To obtain such compounds, a halogen substituent on the piperidine-2-one ring can be converted into an acetyloxy group by treatment with silver acetate in acetic acid or with tetraethylammonium acetate in a suitable solvent. Solvolysis of the acetate with aqueous methanolic sodium hydroxide or methanol in the presence of sodium methoxide will give compound XXVIII wherein $R_5$ and/or $R_6$ is hydroxy or $CH_2OH$. For example, the dibromo-anilide

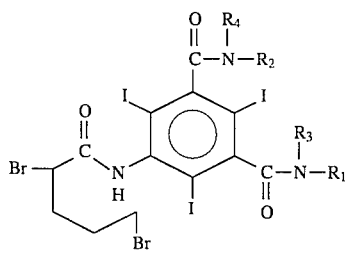

can be ring closed to the 3-bromo-piperidin-2-one

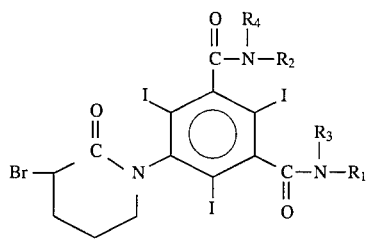

The bromo moiety of compound XXVIIIa can be converted into the acetate and then to the corresponding hydroxy compound by the methods described above.

2,5,dibromopentanoyl bromide used in the preparation of compound XXVIIa is prepared by treating δ-valerolactone with bromine in the presence of red phosphorous. 2,5, dibromopentanoyl bromide is condensed with compound XV to form compound XXVIIa.

An alternate and preferred synthesis of piperdin-2-one compounds of formula I having —OX at the 3 position is described in a copending application entitled "PROCESS FOR PREPARATION OF 5-(2-OXO-1-PIPERIDINYL)-2, 4,6-TRIIODOPHENYL DERIVATIVES" (in U.S. Pat. No. 5,359,077) filed concurrently herewith. That process involves the ring-opening of a tetrahydrofuroyl group

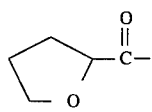

with a Lewis acid, e.g., BBr3, a source of halide or leaving group and optionally a source of oxygen protection, e.g., acetyl anhydride. Subsequent treatment with a base provides compounds having the desired

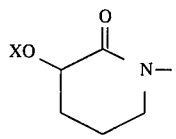

moiety where X is H or an oxygen protecting group. This methodology is described in greater detail in Schemes D–H, below.

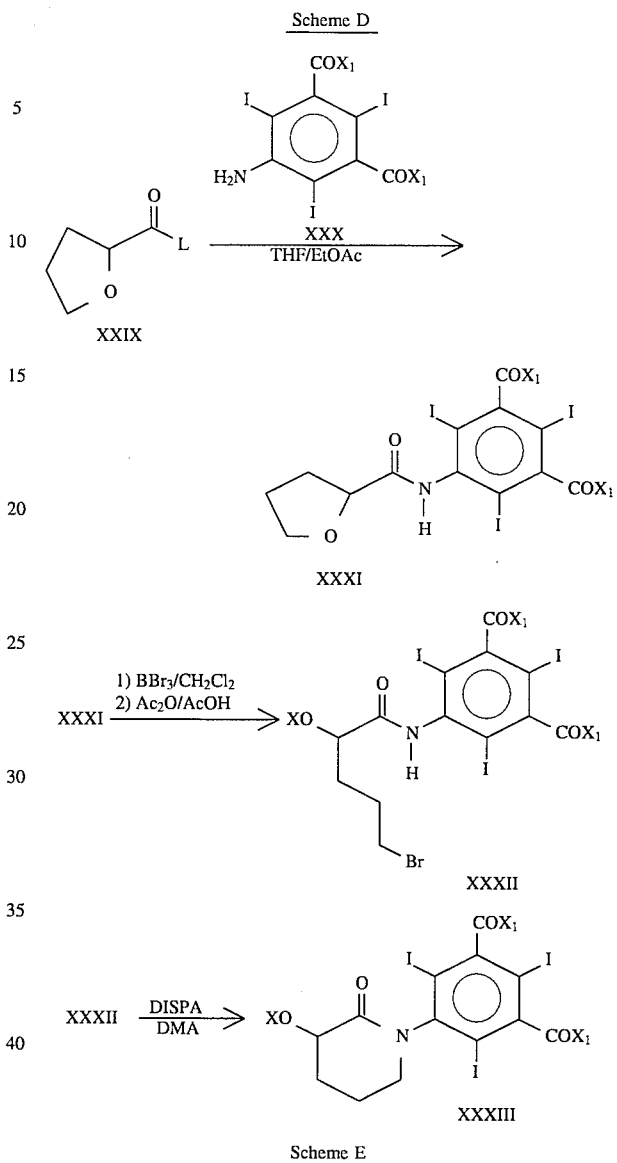

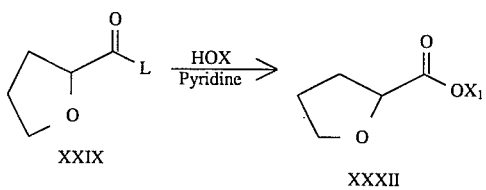

XXXIV $\xrightarrow[\text{(where X is other than —H, e.g., Ac)}]{\text{ZnCL}_2 \\ \text{XOCl}}$ 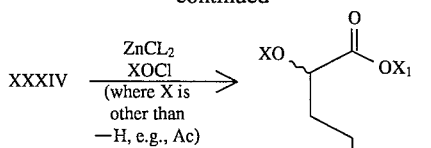 XXXV XXXV $\xrightarrow{\text{reduction}}$ 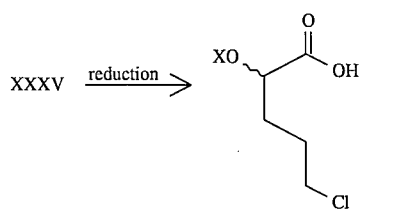 XXXVI XXXVI $\xrightarrow{\text{oxalyl chloride}}$ 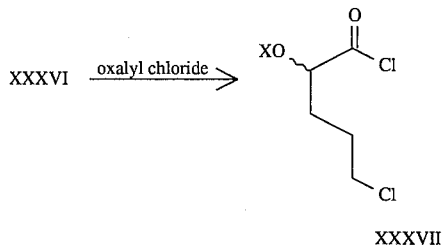 XXXVII XXXVII 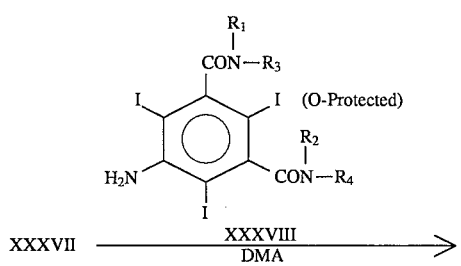 $\xrightarrow[\text{DMA}]{\text{XXXVIII}}$

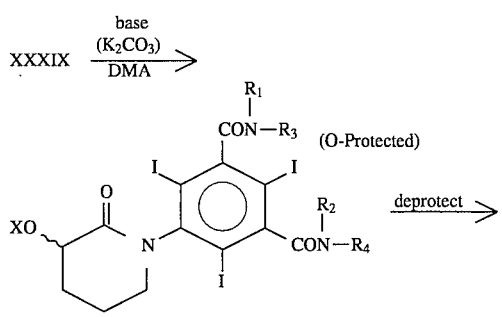 XXXIX

XXXIX $\xrightarrow[\text{DMA}]{\text{base} \\ (\text{K}_2\text{CO}_3)}$ 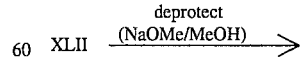 $\xrightarrow{\text{deprotect}}$

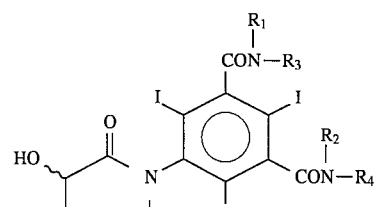

Scheme F

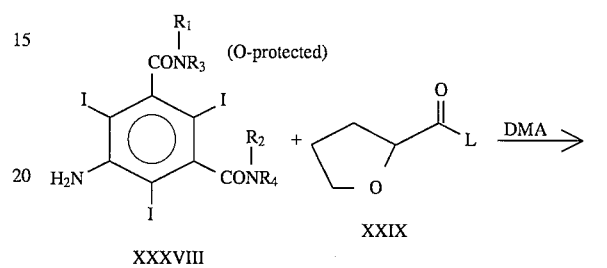 $\xrightarrow{\text{DMA}}$

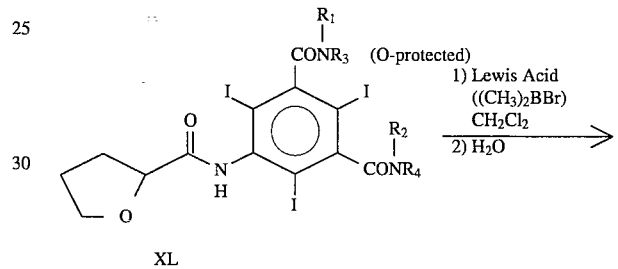 $\xrightarrow[\text{2) H}_2\text{O}]{1)\ \text{Lewis Acid} \\ ((\text{CH}_3)_2\text{BBr}) \\ \text{CH}_2\text{Cl}_2}$

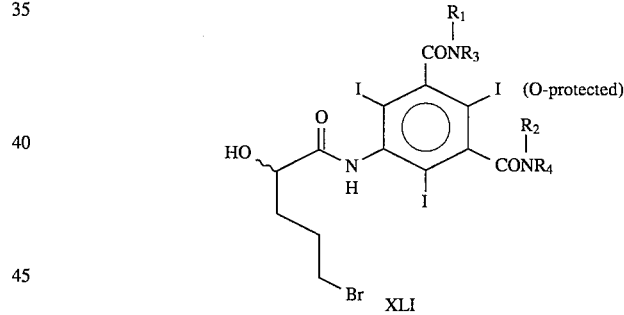 XLI

XLI $\xrightarrow[\text{DMA}]{\text{Base} \\ (\text{K}_2\text{CO}_3)}$ 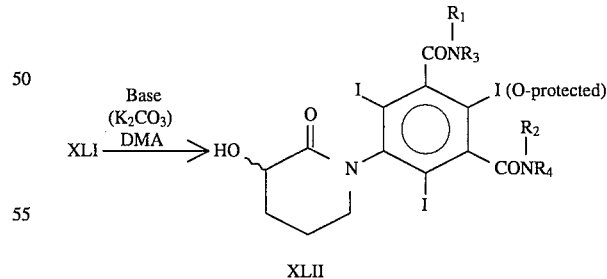 XLII XLII $\xrightarrow{\text{deprotect} \\ (\text{NaOMe/MeOH})}$

Scheme G-1

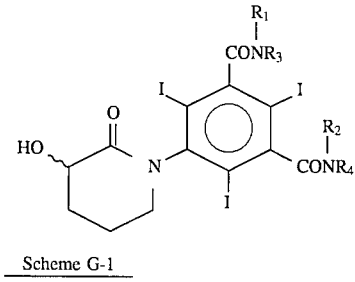

Product of Scheme D

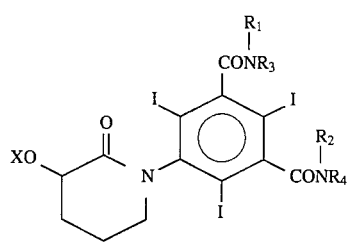

where $R_1 = R_2$; $R_3 = R_4$
XLIII

XLIII →deprotect→

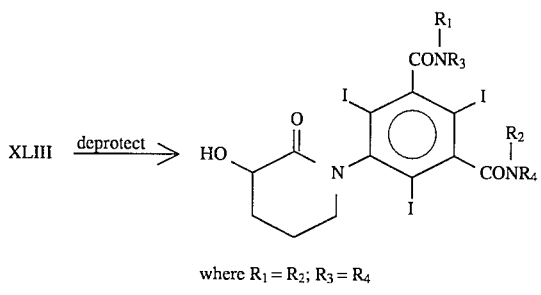

where $R_1 = R_2$; $R_3 = R_4$

Scheme G-2

(a) Product of Scheme D $\xrightarrow{\underset{R_4}{\overset{R_2}{HN-}}}$

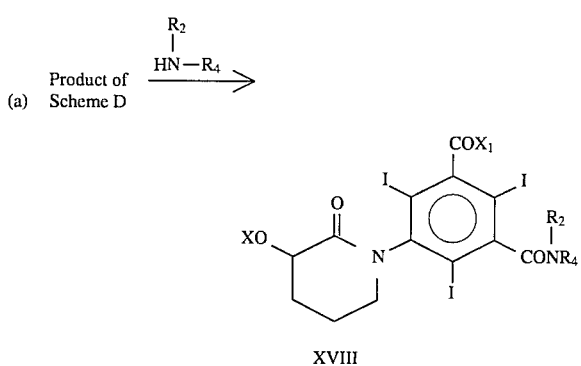

XVIII (b) XVIII $\xrightarrow{\underset{R_3}{\overset{R_1}{HN-}}}$ Ia (where $R_1 \neq R_2$ and/or $R_3 \neq R_4$)

Scheme H

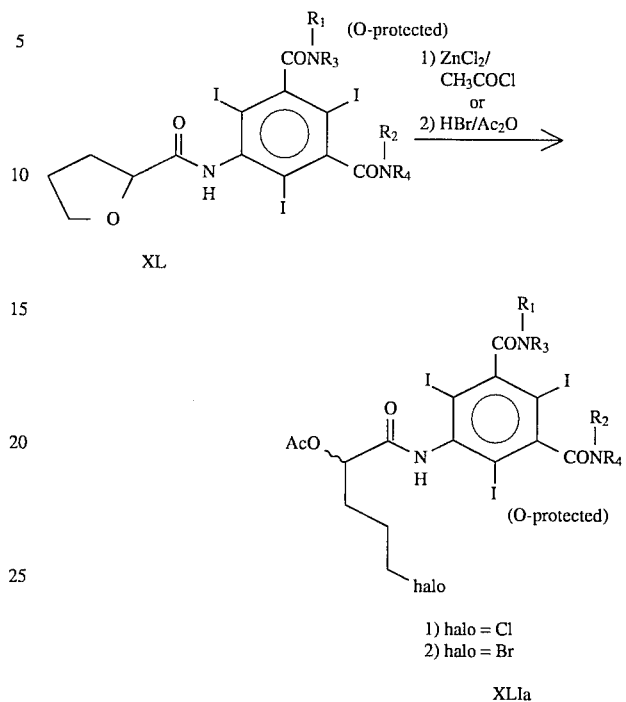

1) halo = Cl
2) halo = Br

XLIa

In Scheme D, compound XXIX, L is a leaving group, e.g., chloro. Accordingly, 2-tetrahydrofuroyl chloride XXIX is readily prepared by reacting 2-tetrahydrofuroic acid neat, or as a solution in dimethylformamide, with oxalyl chloride under nitrogen, preferably at 25° C. Compound XXIX is reacted with amine XXX where $X_1$ is preferably a leaving group, e.g., chloro, in solvents, such as tetrahydrofuran and ethyl acetate, to provide the furancarboxamide XXXI. Compound XXXI is treated with a Lewis acid such as $BBr_3$ in $CH_2Cl$ followed by further treatment with a source of O-protection, $(X)_2O$, such as acetic anhydride and acetic acid, in the same solvent to provide the ring-opened bromopentanamide XXXII. Compound XXXII is then treated with a base, e.g., diisopropylamine, in a solvent, e.g., N,N-dimethylacetamide, preferably under $N_2$ pressure, to provide the ring-closed piperidinyl compound XXXIII. Conversion of XXXIII to compounds of I is described later in Scheme G.

In Scheme E the tetrahydrofuroyl ring is opened prior to coupling with the triiodinated phenyl group. Accordingly, 2-tetrahydrofuroyl chloride XXIX is reacted with HOX, such as benzyl alcohol (where $X_1$ is an oxygen protecting group, e.g., benzyl) in a solvent, e.g., pyridine, to provide XXXIV. Intermediate XXXIV is thereafter treated with a Lewis acid, e.g., $ZnCl_2$ and XOCl (preferably where X is an oxygen protecting group), e.g., acetyl chloride, to provide the chloro-pentanoate intermediate XXXV. Reductive deprotection of XXXV by standard methods, e.g., treatment with $H_2$ in the presence of Pd/C, provides compound XXXVI which is conveniently activated with, for example, oxalyl chloride to provide the chloro-pentanoyl chloride XXXVII. Reaction of XXXVII with a preferably O-protected XXXVIII, i.e., where hydroxy groups in $R_1$–$R_4$ are preferably, for example acetyloxy, provides the benzenedicarboxamide XXXIX. Treatment of XXXIX with a base, e.g., potassium carbonate, in a solvent, e.g., N,N-dimethylacetamide provides the protected products. Standard deprotection of XXXIX, for example, via treatment with NaOMe in a solvent, e.g., methanol, provides compounds of I.

Scheme F is similar to the approach in Scheme D, that is, the tetrahydrofuroyl-containing compound is coupled to the triiodinated phenyl nucleus prior to ring opening. However, unlike Scheme D, Scheme F utilizes a starting compound XXXVIII (preferably O-protected) instead of the bis-acid chloride XXX, i.e., where the

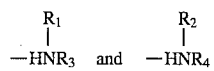

sidechains are already present.

Schemes G-1 and G-2 convert the products of Scheme D to the products of I. When the product of I is desired to be a symmetrical amide (i.e., where $R_1=R_2$ and $R_3=R_4$), the products Scheme D, for example, where $X_1$ is chloro, are reacted with 2 equivalents of

in solvents, e.g., acetonitrile and water and in the presence of an organic base, e.g., triethylamine, as shown in Scheme G-1. Where X is other than hydrogen in the products of XLIII are deprotected, e.g., with sodium hydroxide to provide the desired symmetrical amides.

Scheme G-2 provides unsymmetrical amides of I (i.e., where $R_1 \neq R_2$ and/or $R_3 \neq R_4$) by first reacting the product of Scheme D with 1.1 equivalents of

under conditions as those described in G-1. Intermediate XLIV is thereafter reacted with one-equivalent of

under similar conditions to provide the unsymmetrical amides. Again, as above, if X is other than H, it can be deprotected by known techniques.

For unsymmetrical amides of I where one amide is desired to be a primary amide

where $R_1=R_3=H$) and one is to be a secondary or tertiary amide

where at least one of $R_2, R_4 \neq H$), step (a) is preferably carried out first and thereafter the so-formed intermediate XLIV is reacted with ammonia

where $R_1=R_3=H$) to provide the corresponding products of I.

Scheme H provides a variation in Scheme F by using the optional compound X-O-halogen (i.e., a source of halide and of O-protection) or $(X)_2O$ (which is also described in Scheme D) along with the Lewis acid in treating compound XL. The respective compounds used with the Lewis acids in Scheme H are acetyl chloride and acetic anhydride. These directly provide the acetyloxy substituted derivatives of XLIa in one step.

In the above reactions of Schemes D–H, tetrahydrofuroic acid and oxalyl chloride used to prepare compound XXIX are commercially available. Starting materials XXX and XXXVIII are known and have been described, for example, in EP 431,838.

The compounds of formula I wherein the heterocyclic group is a morpholin-3-one can be prepared by reacting Compound XV with a β-chloroethoxyacetyl halide such as β-chloroethoxyacetyl chloride in dimethylacetamide to yield the anilide of the formula

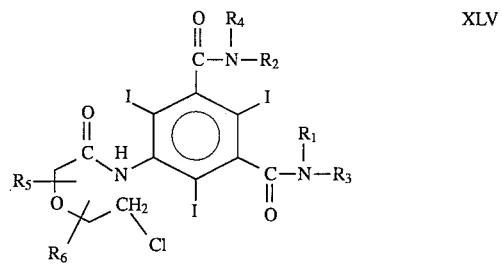

Compound XLV, under basic conditions will undergo cyclization to provide the morpholin-3-one derivative of the formula

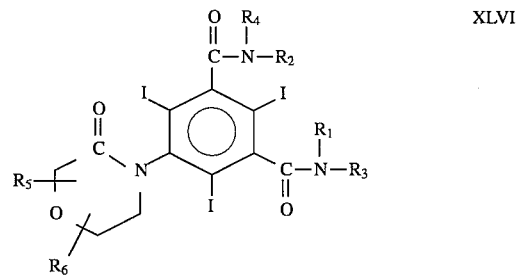

For the preparation of compounds of formula XLVI wherein $R_5$ and $R_6$ are other than hydrogen, appropriate substituted β-chloroethoxyacetyl halides are used.

Alternatively, condensation of substituted allyloxyacetyl of the formula

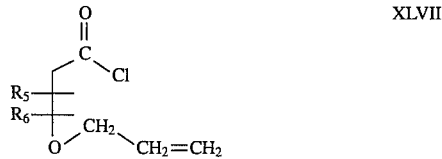

with compound XV will yield the anilide of the formula

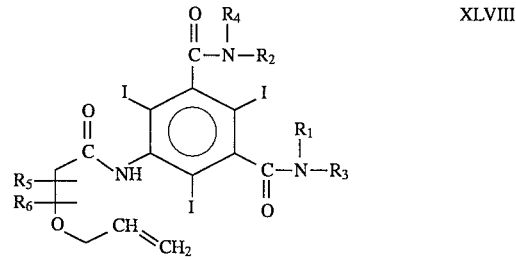

Intramolecular halolactamation under basic conditions by treatment with N-iodosuccinimide yields the corresponding halide of the formula

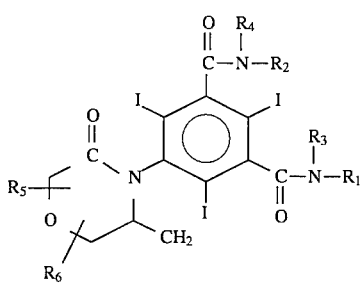

XLIX

This approach provides morpholin-5-one derivatives with a branched halomethyl substituent at the 3-position. The basic conditions are required to avoid the formulation of undesired O-participative ring closure intermediates. In the presence of sodium methoxide N-ring closure is favored over O-ring closure by a factor of approximately 95:5. If the substituents $R_1$, $R_2$, $R_3$ and $R_4$ contain acetyloxy groups, they will be deprotected during the ring closure reaction due to the basic conditions employed. The acetyl groups are reintroduced by subjecting the cyclized product to the treatment with acetic anhydride in pyridine.

An alternative way to prevent the amide oxygen of compound XLVIII from participating in the above cyclization is to transform the amide function into a silyl derivative according to the procedure of S. Knapp, Tetrahedron Letters, 26, p. 1803 (1985).

Acetolysis of compound XLVIII with silver acetate in acetic acid yields the corresponding acetyloxy derivative. Solvolysis of the acetate with sodium methoxide in methanol or with aqueous methanolic sodium hydroxide will yield the hydroxymethyl-morpholinone analog of the formula

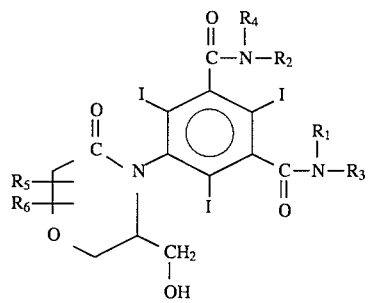

L

The compounds of formula I wherein the heterocyclic group is a pyrimidin-2-one can be prepared by reacting compound XV with the appropriately substituted haloisocyanate of the formula

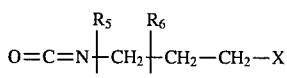

LI wherein X is chloro or bromo to provide the compound of the following formula

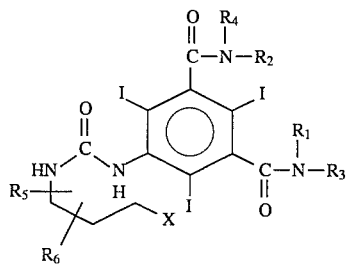

LII

Cyclization in the presence of a base yields the desired pyrimidine 2-one analogs having the formula

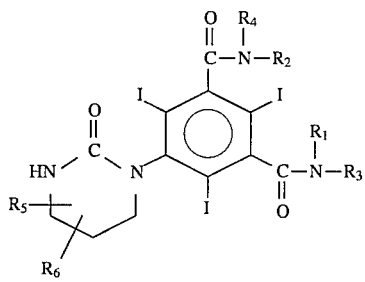

LIII

The compounds of formula I wherein the heterocyclic group is a piperazin-2,5-dione can be prepared by reacting compound XV with a compound of the formula

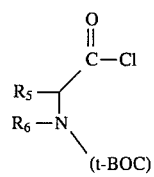

LIV to yield a compound of the formula

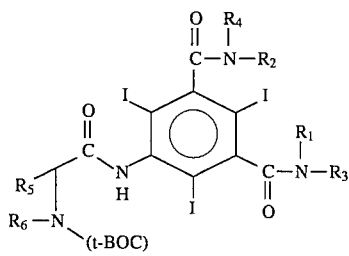

LV

After deprotection of compound LV, the resultant compound can be reacted with chloroacetyl chloride, followed by intramolecular cyclization to yield the desired piperazin-2,5-dione of the formula

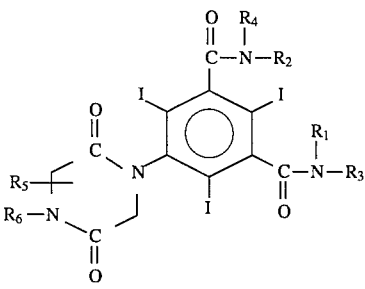

LVI

The compounds of formula I wherein the heterocyclic group is oxazin-2-one can be prepared by reacting compound XV with

to yield a compound of the formula

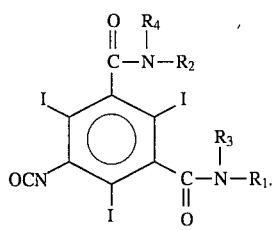 LVII

Treatment of compound LVII with 1-hydroxy-2-(tetrahydropyron-2-yl)oxy-3-chloropropane in the presence of phenylmercuric acetate yields the carbamate of the formula

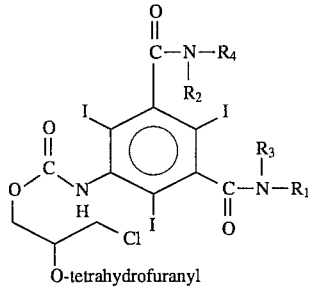 LVIII

O-tetrahydrofuranyl

Cyclization of compound LVIII to the 1,3 oxazin-2-one is accomplished by heating in pyridine or by treatment with sodium hydride in a suitable solvent. The tetrahydropyranyl group is removed by stirring with methanol in the presence of a catalytic amound of p-toluenesulfonic acid to give the desired oxazin-2-one of the formula:

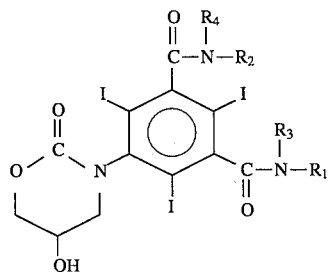 LIX 1-hydroxy-2-(tetrahydropyran-2-yl)oxy-3-chloropropane can be prepared by the following scheme: epichlorohydrin is reacted with acetic acid in the presence of a catalytic amount of iron trichloride to give a mixture of 1-acetyloxy-3-chloropropan-2-ol and 2-acetyloxy-3-chloropropan-1-ol, the major component. The mixture is treated with dihydropyran in the presence of p-toluenesulfonic acid for five hours at 25° C. to give a mixture of 1-acetyloxy-2-(tetrahydropyran-2-yl)oxy-3-chloropropane and 1-(tetrahydropyranyloxy)-2-acetyloxy-3-chloropropane. The mixture is added to a rapidly stirred mixture of aqueous methanol and potassium carbonate at 25° C. and stirred for two hours. Evaporation of the methanol, extraction and drying yields a mixture 1-hydroxy-2-(tetrahydropyran-2-yl)oxy-3-chloropropane and 1-(tetrahydropyran-2-yl)oxy-2-hydroxy-3-chloropropane. Fractional vacuum distillation yields pure 1-hydroxy-2-(tetrahydropyran-2-yl)-oxy-3-chloro-propane since the minor impurity is converted into the more volatile epoxy compound during the distillation procedure.

Alternatively, oxazinone with a 4-hydroxymethyl substituent can be prepared by reacting compound LVII with an appropriately substituted 3,4-epoxybutan-1-ol of the formula

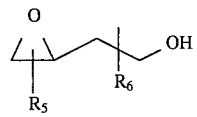 LX in the presence of phenyl mecuric acetate to yield the carbamate of the formula

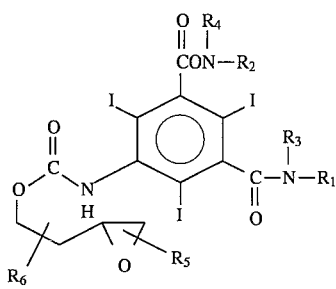 LXI

Heating of compound LXI in pyridine will yield the corresponding oxazin-2-one of the formula

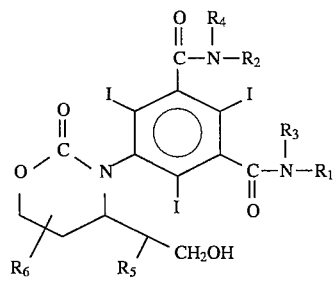 LXII

The compound of formula I wherein the heterocycle is imidazolin-2-one can be prepared by reacting compound LVII with an allyl amine or an allyl amide in order to obtain the following compound:

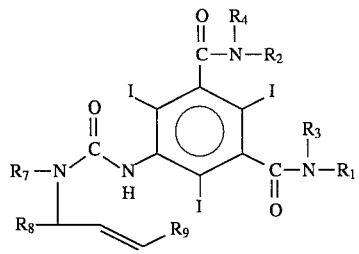 LXIII wherein $R_7$ is hydrogen, lower alkyl or acetyl, $R_8$ and $R_9$ are hydrogen or lower alkyl with the provision that only one of $R_7$, $R_8$ and $R_9$ can be lower alkyl. The mixed urea of compound LXIII can be silyated with trimethylsilyl triflate as can the mixed acyl-urea (when $R_7 = -\overset{\text{O}}{\underset{\|}{C}}-CH_3$)

to give the corresponding O-silyated derivatives which upon treatment with N-iodosuccinimide or iodine leads to the formation of the corresponding iodomethylimidazolin-2-ones of the following formulae

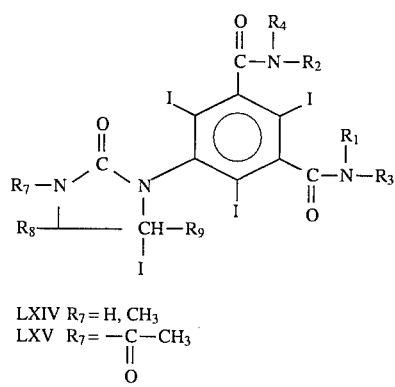

LXIV R$_7$ = H, CH$_3$
LXV R$_7$ = —C—CH$_3$
        ‖
        O

Acetolysis of compound LXIV and LXV using silver acetate/acetic acid or tetraethylammonium acetate results in the corresponding acetyloxymethyl compounds shown in LXVI. Deacetylation will yield the desired compound of formula I, wherein R$_7$ is H or CH$_3$.

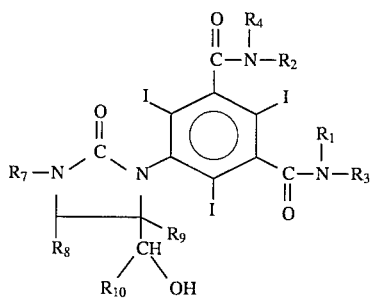

LXVI

The compound of formula I wherein the heterocycle is piperazine-2-one can be prepared by reacting compound XI with a compound of the formula

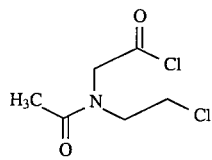

LXVII to yield a compound of the following formula

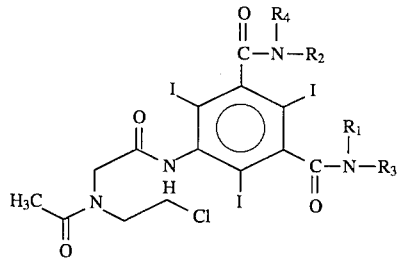

LXVIII

Cyclization in the presence of a base affords the desired piperazine-2-one analogs having the formula

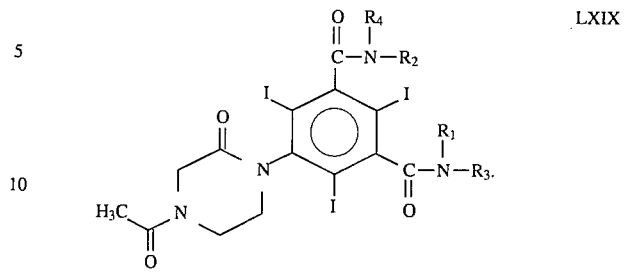

LXIX

The acyclic synthon of formula LXVII can be made by methods described in prior art and shown in the following scheme

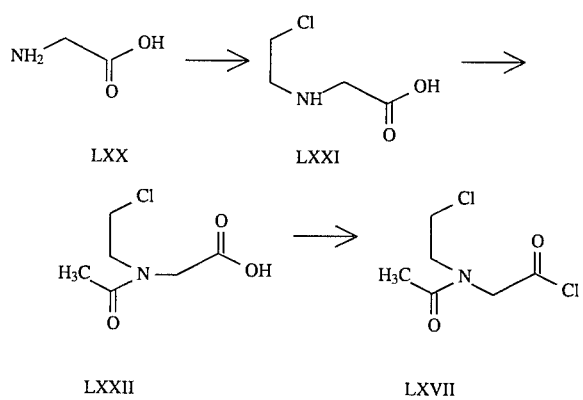

LXX  LXXI

LXXII  LXVII

The compounds of formula I wherein the heterocyclic group is an azepin-2-one can be prepared by reacting compound XV with an appropriately substituted ε-bromohexanoyl bromide of the formula

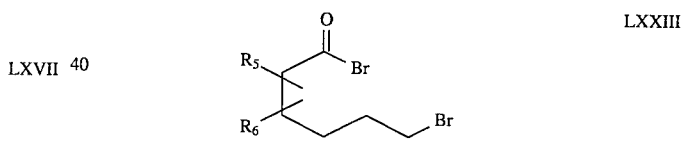

LXXIII in a suitable solvent, such as dimethylacetamide, to yield the corresponding compound of the formula

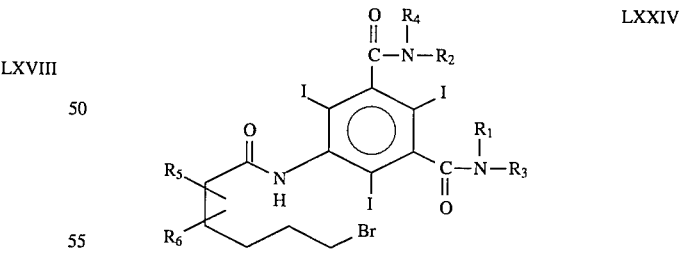

LXXIV which upon treatment with a base, such as potassium carbonate, in a suitable solvent, such as dimethylacetamide, will yield the desired azepin-2-one of the formula

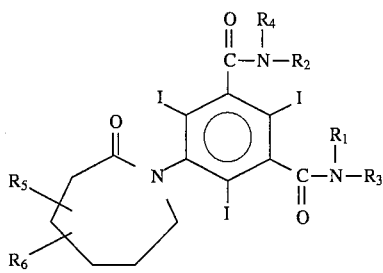

LXXV

When $R_5$ or $R_6$ is hydroxyl or hydroxymethyl in compound LXXV, it is protected as the corresponding acetate or ether, which is eventually deprotected by conventional means. A halogen substituent on the azepin-2-one ring can be converted into an acetyloxy group by treatment with silver acetate in acetic acid or with tetraethylammonium acetate in a suitable solvent. Solvolysis of the acetate with aqueous methanolic sodium hydroxide or methanol in the presence of sodium methoxide will give compound LXXV wherein $R_5$ and/or $R_6$ is hydroxy or $CH_2OH$. For example, the dibromoanilide

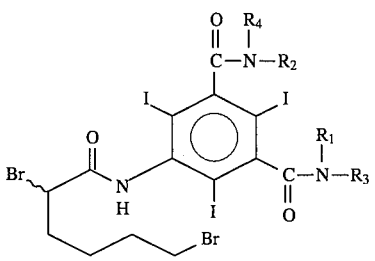

LXXVI can be ring closed to the 3-bromo-azepin-2-one

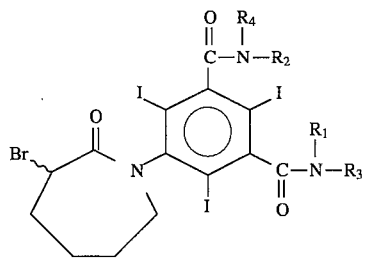

LXXVII

The bromo moiety of compound LXXVII can be converted into the acetate and then to the corresponding hydroxy compound by the methods described above.

2,6-Dibromohexanoyl bromide used in the preparation of compound LXXVI is prepared by treating ε-caprolactone with bromine in the presence of red phosphorus. 2,6-Dibromohexanoyl bromide is condensed with compound XV to form compound LXXVI.

The compounds of the invention are suitable for use in most fields of application in which water soluble radiopaque compounds are necessary, such as vasography, urography, arthrography, and for the visualization of body cavities containing cerebrospinal fluid. When formulated with addition agents which increase the viscosity of the aqueous solutions, they may be employed to advantage for bronchography and hysterosalpingography.

The radio-opaque compounds of the invention are particularly useful as active ingredients of aqueous compositions for visualization of the cardiovascular system and for cerebral angiography. Because of their non-ionic nature, they are suited for visualization of body cavities containing spinocerebral liquor such as in radiculography, ventriculography and myelography.

Aqueous compositions for the applications indicated above may be formulated to contain a single compound of the invention, or more than one compound of the invention, if the individual compounds are very pure.

The radio-opaque compositions of the invention are aqueous solutions containing 15 g and more of the compounds per 100 ml, equivalent to 50 to approximately 500 mg iodine per ml. The more concentrated solutions are generally preferred, and they are applied in a manner generally known and selected according to the body cavity which it intended to visualize. In vasography, the solutions are injected or infused into the vessels, particularly the blood vessels. Intravenous injection is resorted to in urography. For myelography and radiculography, the solutions are instilled after lumbar or suoccipital puncture. The amounts of solution necessary generally are 5 to 15 ml for myelography, 3 to 5 ml for radiculography, and 1 to 2 ml in ventriculography.

The X-ray contrast compositions containing the compounds of the invention as active ingredients are prepared in a very simple manner since no salt-forming or solubilizing ingredients are needed. Any one of the compounds of Examples 1–6 may be dissolved under sterile conditions in the desired amount of double-distilled water, and the solution so obtained is ready to be received in vials and sterilized. The compounds are not decomposed at sterilizing temperatures during the usual sterilizing periods (30 minutes at 120° C. or 60 minutes at 100° C.).

The new heterocycle based non-ionic contrast agents described herein have improved features not present in currently available contrast agents. Their superior stability characteristic, eliminates the need to use organic buffers or carbon dioxide saturation during sterilization of their formulations by autoclaving.

The new heterocycle based non-ionic contrast agents described herein are found to have excellent properties as to tolerance, water solubility, stability, osmolality, viscosity and the like, factors important in angiogrophy and urography.

The compound of Example 8 also exhibits anti-coagulant behavior. This property is desirable in a nonionic x-ray contrast agent that is to be used in angiography. Other compounds of formula I may also possess this anti-coagulant behavior.

The following examples are offered by way of illustration and not by way of limitation. All temperatures are given in centigrade.

EXAMPLE 1

N,N'-Bis(2,3-dihydroxypropyl)-5-[4-(hydroxymethyl)-2-oxo-3-oxazolidinyl]-2,4,6-triiodo-1,3-benzenedicarboxamide

EXAMPLE 1a

[3,5-Bis-[[[2,3-bis(acetyloxy)propyl]amino]carbonyl]2,4,6-triiodophenyl]carbamic acid, oxiranylmethyl ester To a solution of 5-amino-N,N'-bis[2,3-bis-(acetyloxy)propyl-2,4,6-triiodo-1,3-benzenedicarboxamide, (30.00 g, 0.034 mole) in ethyl acetate (300 ml) was added a toluene solution (2 molar) of phosgene (170 ml, 0.34 mole). The flask was stoppered with a rubber septum and wired tightly. The reaction mixture was stirred at 60° C. for 15 hours.

Ethyl acetate and toluene were removed, under vacuum, by slowly raising the temperature to 85°–90°. After removing the solvents, ethyl acetate (150 ml) was added to the residue and was slowly distilled off. This process was repeated twice. The residue containing the isocyanate product was dried in vacuo for 1 h. The crude isocyanate, thus obtained as a colorless solid, was redissolved in ethyl acetate (350 ml) and glycidol (5.4 g, 0.071 mol), followed by phenylmercuric acetate (300 mg), were added to this solution with stirring at room temperature. The reaction mixture was stirred overnight. Undissolved impurities were removed from the reaction mixture by filtration and water (200 ml) was added to the filtrate. The organic layer that separated, was washed with water (2×100 ml) and brine (100 ml). It was dried and the solvent was removed, to obtain the glycidyl carbamate, as a nearly colorless solid (32.00 g). To a solution of this solid is ethyl acetate (150 ml), hexane (10 ml) was added and the solution was allowed to stand in the refrigerator overnight. The solid, thus obtained, was filtered and dried, to obtain the glycidyl carbamate, as a crystalline solid (21.6 g). The mother liquor was concentrated and the resulting solid was crystallized, as described above, to obtain an additional 6.3 g of the product. Both the crops were combined and the resulting solid, upon recrystallization once again from a mixture of ethyl acetate (100 ml) and hexane (10 ml), afforded pure oxiranylmethyl [3,5-bis[[[2,3-bis(acetyloxy)propyl]amino]carbonyl]-2,4,6-triiodophenyl]carbamate, as a white crystalline powder (25.6 g, yield 76.5%), mp, 142°–145°.

EXAMPLE 1B

N,N'-Bis[2,3-bis)acetyloxy)propyl]-5-(4-hydroxymethyl)-2-oxo-3-oxazolidinyl]-2,4,6-triiodo-1,3-benzenedicarboxamide A solution of the oxiranylmethyl ester of Example 1a (30.00 g, 0.030 mole) in freshly distilled anhydrous pyridine (300 ml) was heated at 75° C. The reaction was found to have gone to completion in 2.5 h. Pyridine was removed from the reaction mixture in a rotary evaporator at 50° C. and the residue was co-evaporated twice with toluene (100 ml), to remove residual pyridine. The solid, thus obtained, was dissolved in ethyl acetate (100 ml) and, then, precipitated by pouring into toluene (200 ml). The solid was filtered and dried to afford a white powder. The product was crystallized from aqueous methanol. N,N'-bis[2,3-bis(acetyloxy)propyl]-5-[4-hydroxymethyl)-2-oxo-3-oxazolidinyl]-2,4,6-triiodo1,3-benzenedicarboxamide was obtained as colorless needles. A second crop of 4.6 g was further obtained from the mother liquor. Total yield 75%; mp, 278°–80°.

EXAMPLE 1c

N,N'-Bis(2,3-dihydroxypropyl)-5-[4-(hydroxymethyl)-2-oxo-3-oxazolidinyl]-2,4,6-triiodo-1,3-benzenedicarboxamide To a solution of N,N'-Bis[2,3-bis(acetyloxy)propyl]-5-[4-(hydroxymethyl)-2-oxo-3-oxazolidinyl]2,4,6-triiodo-1,3-benzenedicarboxamide of Example 1b 5 (18.00 g, 0.0184 mole) in anhydrous methanol (180 ml) was added a methanolic solution of sodium methoxide (1.08 g, 0.02 mole) and the mixture was stirred for 1 h. Dowex-50 (H$^+$) resin was added to this solution until the pH was brought down to approximately 7.00. The resin was filtered off, the methanol removed in a rotary evaporator and the resulting syrupy material dissolved in water (150 ml). The solution was decolorized by boiling for 15 minutes with Darco (200 mg). It was then filtered and solvent removal afforded a colorless glass, which was dried in a vacuum oven for 24 hours. The product (14.1 g, yield 95%), thus obtained, had a purity of 99.67%.

The material was further purified by low pressure reverse phase column chromatography, using the CHP-20 resin. The product (4.7 g) was obtained as a white powder. HPLC analysis of this material revealed that only the hydrophobic impurity had been removed by this procedure. The hydrophilic impurity was, however, removed by crystallization from water, affording pure N,N'-bis-(2,3-dihydroxypropyl)-5-[4-(hydroxymethyl)-2-oxo-3-oxazolidinyl]-2,4,6-triiodo-1,3-benzenedicarboxamide, (4.15 g, 99.86%), as fine white needles. mp, 315°–320° (d.) Recrystallization was also achieved from a mixture of isopropanol and water.

EXAMPLE 2

N,N'-bis(2,3-dihydroxypropyl)-5-[(R)-[4-hydroxymethyl)-2-oxo-3-oxazolidinyl]-2,4,6-triiodo-1,3-benzenedicarboxamide

EXAMPLE 2a

[3,5-Bis-[[[2,3-bis(acetyloxy)propyl]aminocarbonyl[-2,4,6-triiodophenyl]carbamic acid,S-oxiranylmethyl ester To a solution of 5-amino-N,N'-bis(2,3-bis(acetyloxy)propyl]-2,4,6-triiodo-1,3-benzenedicarboxamide (8.10 g, 0.0093 mol) in ethyl acetate (50 ml) was added a toluene solution (2 molar) of phosgene (Fluka AG) (55 ml, 0.110 mol). The flask was stoppered with a rubber septum and wired tightly. The reaction mixture was stirred at 60°. The isocyanate formation was found to be complete in 18 h. Ethyl acetate and toluene were removed under vacuum at 80° C. After removing the solvents, ethyl acetate (100 ml) was added to the residue and it was slowly distilled off. This process was repeated twice. The distillation assembly was removed and the residue containing the product was dried in vacuo for 1 h. The isocyanate obtained as a beige solid, was redissolved in ethyl acetate (350 ml) and, then, treated with S-glycidol (84.6% optically pure by [a]$_D$ measurement, 1.4 ml, 0.021 mol) and phenylmercuric acetate (0.145 g). The reaction mixture was stirred for 48 h. at room temperature. Water (100 ml) was added to the light yellow solution, the organic layer separated, and a small amount of insoluble material that was present was filtered off. The organic layer was then washed with water (2×350 ml), and brine (1×100 ml). It was dried and the solvent removed to obtain the crude carbamate as a beige solid (9.00 g). The solid was dissolved in ethyl acetate (20 ml) and filtered once again. The residue obtained by solvent removal was purified by silica gel column chromatography to obtain [3,5-Bis-[[[2,3- bis(acetyloxy)propyl]aminocarbonyl[-2,4,6-triiodophenyl]carbamic acid, S-oxiranylmethyl ester (5.05 g, 60%) as a colorless glassy solid. m.p. 115°–118°.

EXAMPLE 2b

N,N'-Bis[2,3-bis(acetyloxy)propyl]-5-[4-(R)-(hydroxymethyl)-2-oxo-3-oxazolidinyl]-2,4,6-triiodo-1,3-benzenedicarboxamide A solution of the S-oxiranylmethyl ester of Example 2a (2.45 g, 0.0025 mol) in freshly distilled anhydrous pyridine (25 ml) was heated at 60° for 2. h. Pyridine was removed in a rotary evaporator and the residue was co-evaporated with toluene (3×20 ml). The resulting orange solid was purified by silica gel column chromatography to obtain N,N'-Bis[2,3-bis(acetyloxy)propyl]-5-[4-(R)-(hydroxymethyl)-2-oxo-3-oxazolidinyl]-2,4,6-triiodo-1,3benzenedicarboxamide as a colorless glassy solid, (1.68 g, 68.6%).

EXAMPLE 2c

N,N'-Bis[2,3-bis(acetyloxy)propyl]-5-(4)-(R)-(hydroxymethyl)-2-oxo-3-oxazolidinyl]-2,4,6-triiodo-1, 3-benzenedicarboxamide To a solution of N,N'-Bis[2,3-bis(acetyloxy)propyl]-5-(4)-(R)-(hydroxymethyl)-2-oxo-3-oxazolidinyl]-2,4,6-triiodo-1,3-benzenedicarboxamide of Example 2b (0.410 g, 0.51 mmol) in anhydrous methanol (7 ml) was added a methanolic solution of sodium methoxide (1.18 ml, 1 M solution) and the mixture was stirred at room temperature for 1 h. The methanol was then removed on the rotary evaporator and water (8 ml) was added to redissolve the white residue. Dowex-50 (H$^+$) was added to this solution portionwise to bring the pH down to approximately 7.0. The Dowex-50 resin was filtered off, water was removed on the rotary evaporator, and the white solid dried in vacuo at 60° over P$_2$O$_5$. The solid thus obtained (0.350 g) was redissolved in water (0.5 ml), seeded with a tiny crystal of the racemate and left overnight. The crystallized product was filtered, washed with cold water and dried overnight over P$_2$O$_5$ to obtain N,N'-Bis[2,3-bis(acetyloxy)propyl]-5-(4)-(R)-(hydroxymethyl)-2-oxo-3-oxazolidinyl]-2,4,6-triiodo-1,3-benzenedicarboxamide as white crystalline needles (0.32 g, 84%).

EXAMPLE 3

N,N'-Bis[2-hydroxy-1-(hydroxymethyl)ethyl]-5-[4-(hydroxymethyl)-2-oxo-3-oxazolidinyl]-2,4,6-triiodo-1,3-benzenedicarboxamide EXAMPLE 3a

[3,5-Bis[[[2-(acetyloxy)-1-[(acetyloxy)methyl]ethyl]amino]carbonyl]-2,4,6-triiodophenyl]carbamic acid, oxiranylmethyl ester A solution of the N,N'-bis[2-(acetyloxy)l[(acetyloxy)-methyl]ethyl]-5-amino-2,4,6-triiodo-1,3-benzenedicarboxamide (14.4 g, 16.4 mmol) in 1,4-dioxane (150 ml) was added to a toluene solution (2.0 m) of phosgene (124 ml, 248 mmol). The flask was stoppered and wired tightly. This mixture was then heated at 60° C. under stirring overnight.

The solvents were removed by slowly raising the temperature to 85°–90° C. in vacuo. The solid residue obtained was redissolved in 1,4-dioxane (80 ml) and again freed of the solvent. This process was repeated four times. The distillation assembly was removed and the residue containing the isocyanate intermediate was dried in vacuo for 30 minutes.

The isocyanate intermediate, thus obtained as a light yellow colored solid, was redissolved in 1,4-dioxane (125 ml). The dioxane solution was treated with glycidol (3.1 g, 2.7 ml, 41.3 mmol). A catalytic amount of phenylmercuric acetate (170 mg) was added and the reaction mixture stirred at room temperature for 17 h. 1,4-Dioxane was removed at 45° on a rotavapor under diminished pressure. The resulting light yellow solid was dissolved in acetonitrile and the solution was extracted with saturated aqueous sodium chloride (3×100 ml). The organic layer was dried, filtered, and the solvent removed to obtain the title compound as a yellow solid (15.7 g).

The crude compound was purified by crystallization from boiling acetonitrile (200 ml) to obtain oxiranylmethyl [3,5-bis[[[2-(acetyloxy)-1-[(acetyloxy)methyl]ethyl]amino]carbonyl]-2,4,6-triiodophenyl]carbamate as an off-white solid. (12.1 g; yield 75%). M.P. 228°6–230°.

EXAMPLE 3b

N,N'-Bis[2-(acetyloxy)-1-[(acetyloxy)methyl]ethyl]-5-[4-(hydroxymethyl)-2-oxo-3-oxazolidinyl]-2,4,6-triiodo-1,3 -benzenedicaboxamide A solution of oxiranylmethyl [3,5-bis[[[2-(acetyloxy)-1-[(acetyloxy)methyl]amino]carbonyl]-2,4,6-triiodophenyl]carbamate of Example 3a (12.1 g, 12.4 mmol) in freshly distilled anhydrous pyridine (120 ml) was heated at 75° C. for 45 minutes. Pyridine was removed under diminished pressure at 45° C. and the residue was co-evaporated twice with toluene (75 ml). The solid thus obtained was dissolved in ethyl acetate (250 ml) and the solution was washed with H$_2$O (1×100 ml). The organic layer was dried (MgSO$_4$). It was then filtered and the solvent removed to obtain the title compound as a yellow solid (9.2 g).

The crude compound was purified by crystallization from a minimum amount of boiling methanol (30 ml). N,N'-Bis[2-(acetyloxy)-1-[(acetyloxy)methyl]ethyl]-5-[4-(hydroxymethyl)-2-oxo-3-oxazolidinyl]-2,4,6-triiodo-1,3-benzenedicarboxamide was obtained, after filtration and drying, as a white crystalline powder (first crop 4.12 g; second crop 1.45 g). These two crops were combined and recrystallized from methanol once again to obtain the oxazolidin-2-one (4.90 g; yield 40.6%) with a purity of 98.7%, as shown by HPLC, m.p. 235°–240°.

Further crops of the product amounting to 3.57 g were obtained form the original mother liquor. TLC indicated an approximate purity of 95%, the impurities consisting of two more polar compounds.

EXAMPLE 3c

N,N'-Bis[2-Hydroxy-1-(hydroxymethyl)ethyl]-5-[4-hydroxymethyl)-2-oxo-3-oxazolidinyl]-2,4,6-triiodo-1,3-benzenedicarboxamide To a solution of N,N'-Bis[2-(acetyloxy)-1-[acetyloxy)methyl]ethyl]-5-[4-(hydroxymethyl)-2-oxo-3-oxazolidinyl]-1,3-benzenedicarboxamide of example 3b (4.2 g, 4.3 mmol) in anhydrous methanol (55 ml) was added a 1 M solution of sodium methoxide in methanol (10 ml) at 0° C. The slurry was stirred at room temperature for 1 h. TLC analysis of the reaction mixture revealed that the deacetylation was complete. Dowex-50-(H$^+$) resin was added to the reaction mixture until the pH was brought down to 7. The resin was filtered and the methanol removed in a rotavapor. The resulting solid reside (3.43 g) was dissolved in H$_2$O (250 ml) and the solution decolorized by boiling for 15 minutes with darco (200 mg). It was then filtered and removal of the solvent afforded a colorless glass which was dried in a vacuum oven for 24 h. The product (3.2 g; yield 92%),. thus obtained, had a purity of 99.69%, as determined by HPLC.

This product was further purified by low pressure reverse phase chromatography over CHP-20P resin to obtain the pure title compound N,N'-bis[2-hydroxy-1-(hydroxymethyl)ethyl]-5-[4-hydroxymethyl)-2-oxo-3-oxazolidinyl]-2,4,6- triiodo-1,3-benzenedicarboxamide (6.2 g, 90% recovery), as a snow-white, glassy solid. HPLC analysis revealed that this sample had negligible amounts of any detectable impurities.

The product was further purified by crystallization from aqueous isopropanol and obtained as colorless clusters of needles.

EXAMPLE 4

N,N'-Bis-[2-hydroxy-1-(hydroxymethyl)ethyl]-5-[3-hydroxy-2-oxo-1-pyrrolidinyl]-2,4,6-triiodo-1,3-benzenedicarboxamide

EXAMPLE 4a

N,N'-Bis-[2-acetyloxy-1-(acetyloxymethyl)ethyl]-5-[3-bromo-2-oxo-1-pyrrolidinyl]-2,4,6-triiodo-1,3-benzenedicarboxamide A solution of N,N'-bis-[2-acetyloxy-1-(acetyloxymethyl)ethyl]-5-[amino]-2,4,6-triiodo-1,3-benzenedicarboxamide, (8.73 g, 10 mmol) in dry N,N-dimethylacetamide (100 ml) was treated with 2,4-dibromobutyroyl bromide (4.017 g, 13 mmol) under nitrogen and the mixture was stirred for 13 hours at 25° C. The dimethylacetamide was removed by distillation at 55°–60° C. under high vacuum. The resulting thick paste was dissolved in dry N,N-dimethylacetamide (160 ml) and potassium carbonate (1.80 g, 13 mmol) was added. The mixture was stirred for 60 minutes. An additional portion of potassium carbonate (1.80 g, 13.0 mmol) was added and the mixture stirred for 80 minutes. The suspended salts were filtered off and the volume of the reaction mixture was reduced to about 80 ml by vacuum distillation at 0.05–0.10 mm/Hg. The residual solution was poured slowly with rapid stirring into ice-water (900 ml). The resulting mixture was stirred overnight at 0° C. and then filtered. The collected precipitate was dried in a vacuum desiccator ($P_2O_5$) and then crystallized from acetonitrile to give an off-white powder. This product was treated with acetic anhydride (30 ml) and pyridine (42 ml) for 32 hours at 25°, after which the volatile components were completely removed under high vacuum to obtain N,N'-bis-[2-acetyloxy-1-(acetyloxymethyl)ethyl]-5-[3-bromo-2-oxo-1-pyrrolidinyl]-2,4,6-triiodo-1,3-benzenedicarboxamide as a white powder (4.67 g, 45% yield), m.p. 232°–234°.

EXAMPLE 4b

N,N'-Bis-[2-acetyloxy-1-(acetyloxymethyl)ethyl]-5-[3-acetyloxy-2-oxo-1-pyrrolidinyl]-2,4,6-triiodo-1,3-benzenedicarboxamide N,N'-bis-[2-acetyloxy-1-)acetyloxymethyl)ethyl]-5-[3-bromo-2-oxo-1-pyrrolidinyl]-2,4,6-triiodo-1,3-benzenedicarboxamide (4.00 g, 3.92 mmol) of example 4a was dissolved in glacial acetic acid (40 ml) and treated with silver acetate (3.25 g, 19.50 mmol) at 133°–135° for 26 hours under a nitrogen atmosphere. The suspended solids were filtered off and the solvent was removed in vacuo. The resulting crude residue was treated with acetic anhydride (30 ml) and pyridine (42 ml), after which the volatile components were completely removed under high vacuum. The resulting product was purified by silica gel flash chromatography to obtain N,N'-bis-[2-acetyloxy-1-(acetyloxymethyl)ethyl]-5-[3-acetyloxy-2-oxo-1-pyrrolidinyl]-2,4,6-triiodo-1,3-benzenedicarboxamide as a pale orange foam (3.20 g, 82% yield).

EXAMPLE 4c

N,N'-Bis-[2-hydroxy-1-(hydroxymethyl)ethyl[-5-[3-hydroxy-2-oxo-1-pyrrolidinyl]-2,4,6-triiodo-1,3-benzenedicarboxamide N,N'-Bis-[2-acetyloxy-1-(acetyloxymethyl)ethyl]-5-[3-acetyloxy-2-oxo-1-pyrrolidinyl]-2,4,6-triiodo-1,3-benzenedicarboxamide of example 4b (2.78 g, 2.78 mmol) was treated with a solution of sodium methoxide in methanol, prepared by the dissolution of sodium (0.032 g, 1.39 mmol) in dry methanol (13 ml), for 4 hours at 25° under an atmosphere of nitrogen to obtain a single major product. The mixture was neutralized to pH 6.98 using Dowex-50 resin ($H^+0$ form). Filtration of the mixture and evaporation of the solvent gave an orange foamy product (1.89 g), which was purified by low pressure reverse phase column chromatography over CHP-20 resin to obtain N,N'-Bis-[2-hydroxy-1-(hydroxymethyl)ethyl]-5-[3-hydroxy-2-oxo-1-pyrrolidinyl]-2,4,6-triiodo-1,3-benzenedicarboxamide as a white foam (1.54 g, 70% yield).

EXAMPLE 5

N,N'-Bis-[2,3-dihydroxypropyl]-5-[3-hydroxy-2-oxo-1-pyrrolidinyl]-2,4,6-triiodo-1,3-benzenedicarboxamide

EXAMPLE 5a

N,N'-Bis-[2,3-diacetyloxypropyl]-5-[3-bromo-2-oxo-1-pyrrolidinyl]-2,4,6-triiodo-1,3-benzenedicarboxamide A solution of N,N'-bis-[2,3-diacetyloxypropyl]-5-amino-2,4,6-triiodo-1,3-benzenedicarboxamide (8.73 g, 10 mmol) in N,N-dimethylacetamide (100 ml) was treated with 2,4-dibromobutyroyl bromide (4.02 g, 13.0 mmol) under an atmosphere of nitrogen and the reaction mixture was stirred for 50 hours at ambient temperature. The mixture was then treated with ground potassium carbonate (1.65 g, 12.0 mmol) and stirred for 30 minutes at ambient temperature. An additional portion (1.65 g, 12.0 mmol) of finely ground potassium carbonate was added and the mixture was stirred for 1.9 hours. The suspended salts were filtered and the solvent was evaporated to obtain a brown oil. This crude product was purified by silica gel flash chromatography to isolate N,N'-Bis-[2,3-diacetyloxypropyl]-5-[3-bromo-2-oxo-1-pyrrolidinyl]-2,4,6-triiodo-1,3-benzenedicarboxamide, as a white powder (7.28 g, 71% yield), m.p. 110°–112°.

EXAMPLE 5b

N,N'-Bis-[2,3-diacetyloxypropyl]-5-[3-acetyloxy-2-oxo-1-pyrrolidinyl]-2,4,6-triiodo-1,3-benzenedicarboxamide N,N'-Bis-[2,3-diacetyloxypropyl]-5-[3- bromo-2-oxo-1-pyrrolidinyl]-2,4,6-triiodo-1,3-benzenedicarboxamide of example 5a, (6.43 g, 6.30 mmol) was dissolved in glacial acetic acid (63 ml) and then treated with silver acetate (4.21 g, 25.21 mmol) at reflux under nitrogen for 26 hours. The reaction mixture was cooled to room temperature and the solids filtered off. The solvent was evaporated in vacuo and the residue was partitioned between ethyl acetate and brine. The organic layer was dried and removal of the solvent afforded the crude product as a colored foam. Purification by silica gel flash chromatography furnished N,N'-bis-[2,3- diacetyloxypropyl]-5-[3-acetyloxy-2-oxo-1-pyrrolidinyl]-2, 4,6-triiodo-1,3-benzenedicarboxamide as an off-white foam (4.45 g, 71% yield).

EXAMPLE 5 c

N,N'-Bis-[2,3-dihydroxypropyl]-5-[3-hydroxy-2-oxo-1-pyrrolidinyl]-2,4,6-triiodo-1,3-benzenedicarboxamide N,N'-Bis-[2,3-diacetyloxypropyl]-5-[3-acetyloxy-2-oxo-1-pyrrolidinyl]-2,4,6-triiodo-1,3-benzenedicarboxamide of example 5b (4.20 g, 4.20 mmol) was treated with a 0.105 M solution of methanolic sodium methoxide [prepared by the addition of Na metal (48 mg, 2.10 mmol) to dry methanol (20 ml)] under a nitrogen atmosphere for 2.5 hours. The pH was then adjusted to 6.70 using Dowex-50 resin ($H^+$ form) and AG-1 ($OH^-$ form) as necessary. The resin was removed and the solvents evaporated to give a yellow oil. This product was dissolved in 20 ml of deionized water and the pH adjusted to 6.98 by the addition of AG-1 ($OH^-$1 form) resin. The resin was filtered off and the filtrate containing the crude product was purified by low pressure reverse phase column chromatography using a CHP-20 resin to obtain N,N'-bis-[2,3-dihydroxypropyl]-5-[3-hydroxy-2-oxo-1-pyrrolidinyl]-2,4,6-triiodo-1,3-benzenedicarboxamide as a white foam (2.36 g, 71% yield).

EXAMPLE 6

5-[2-(hydroxymethyl)-5-oxo-1-pyrrolidinyl]-N,N'-bis(2,3-dihydroxypropyl)-2,4,6-triiodo-1,3-benzenedicarboxamide

EXAMPLE 6a

N,N'-Bis[2,3-bis(acetyloxy)propyl]-2,4,6-triiodo-5-[(1-oxo-4-pentenoyl)amino]-1,3-benzenedicarboxamide 4-Pentenoyl chloride (7.44 g, 62 mmol) was added to a stirred solution of 5-amino-N,N'-bis-[2,3-bis(acetyloxy)propyl]-2,4,6-triiodo-1,3-benzenedicarboxamide (21.8 g, 25 mmol) in dimethylacetamide (150 ml) at room temperature and the mixture was stirred for 16 hours. Dimethylacetamide was removed in vacuo and the residue dissolved in ethyl acetate (250 ml). The solution was washed with aqueous sodium bicarbonate (10%, 100 ml) and water (2×100 ml). The organic layer was dried and the solvent removed to obtain the crude product as an off-white solid. Purification by crystallization from a mixture of ethyl acetate (250 ml) and hexane (50 ml) afforded N,N'-bis[2,3-bis(acetyloxy)propyl]-2,4,6- triiodo-5-[(1-oxo-4-pentenoyl)amino]-1,3-benzenedicarboxamide as a fine powder (21.3 g, yield 89%).

EXAMPLE 6b

N,N'-Bis[2,3-bis(acetyloxy)propyl]-5-[2-(iodomethyl)-5-oxo-1-pyrrolidinyl]-2,4,6-triiodo-1,3-benzenedicarboxamide To a solution of N,N'-bis[2,3-bis(acetyloxy)propyl]-2,4,6-triiodo-5-[(1-oxo-4-pentenoyl)amino]-1,3-benzenedicarboxamide of example 6a (19.1 g, 20 mmol) in methanol (200 ml) was added a solution of sodium methoxide in methanol, prepared by dissolving sodium (1.38 g, 60 mmol) in methanol (30 ml). The mixture was stirred for 1 hour. The solvent was removed in vacuo and the residue was dissolved in a mixture of methanol and water (1:1, v/v; 200 ml). N-Iodosuccinimide (13.3 g, 60 mmol) was added and the mixture stirred at room temperature for 48 hours. The solvents were distilled off and the residue azeotroped with pyridine (3×100 ml). The residue was dissolved in pyridine (150 ml) and treated with acetic anhydride (20.4 g, 200 mmol) with stirring for 17 hours at room temperature. The excess of pyridine and acetic anhydride were removed in vacuo, the residue dissolved in ethyl acetate (250 ml), and the resulting solution washed successively with water (200 ml), aqueous sodium thiosulfate (25%, 2×125 ml), and water (2×150 ml). The organic layer was dried and removal of the solvent afforded the product as a light yellow glassy solid (20.2 g). The crude product was purified by column chromatography over silica gel to obtain N,N'-bis[2,3-bis(acetyloxy)propyl]-5-[2-(iodomethyl)-5-oxo-1-pyrrolidinyl]-2,4,6-triiodo-1,3-benzenedicarboxamide as a glassy solid (13.8 g, yield 64%).

EXAMPLE 6c

5-[2-[(Acetyloxy)methyl-5-oxo-1-pyrrolidinyl]-N,N'-bis(acetyloxy)propyl]-2,4,6-triiodo-1,3-benzenedicarboxamide To a solution of N,N'-bis[2,3-bis(acetyloxy)propyl]-5-[2-(iodomethyl)-5-oxo-1-pyrrolidinyl]-2,4,6-triiodo-1,3-benzenedicarboxamide of example 6b (13.2 g, 150 mmol) in glacial acetic acid (165 ml) was added silver acetate (6.00 g, 35 mmol), and the mixture stirred at 100° C. for 16 hours. The insoluble materials were filtered off, acetic acid removed in vacuo at 60°, and the residue dissolved in a mixture of ethyl acetate (200 ml) and water (100 ml). The ethyl acetate layer was dried and removal of the solvent afforded the crude product as a light pink colored solid. This material was purified by column chromatography over silica gel to obtain 5-[2-[(acetyloxy)methyl-5-oxo-1-pyrrolidinyl]-N,N'-bis(acetyloxy)propyl]-2,4,6-triiodo- 1,3-benzenedicarboxamide as a light pink glassy solid (8.5 g, yield 79%).

EXAMPLE 6d

5-[2-(Hydroxymethyl)-5-oxo-1-pyrrolidinyl]-N,N'-bis(2,3-dihydroxypropyl)-2,4,6-triiodo-1,3-benzenedicarboxamide A solution of 5-[2-[(acetyloxy)methyl-5-oxo-1-pyrrolidinyl N,N'-bis(acetyloxy)propyl]-2,4,6-triiodo-1,3-benzenedicarboxamide of example 6c (5.06 g, 5 mmol) in methanol (50 ml) was treated with a solution of sodium methoxide in methanol, prepared from sodium (115 mg, 5 mmol) and methanol (5 ml). The solution was stirred at room temperature for 1 hour. The pH of the solution was then adjusted to 7 and the solvent removed in vacuo to obtain the crude product. Purification by low pressure reverse phase column chromatography using the CHP-20 resin afforded 5-[2-(hydroxymethyl)-5-oxo-1-pyrrolidinyl]-[N,N'-bis(2,3-dihydroxypropyl]-2,4,6-triiodo-1,3-benzenedicarboxamide as a colorless solid (3.2 g, yield 83%).

This glassy product was crystallized from n-butanol to obtain the title compound as a microcrystalline white powder.

EXAMPLE 7

N,N'-Bis[2-Hydroxy-1-(hydroxymethyl)ethyl-5-[3-(hydroxymethyl) -5-oxo-4-morpholinyl]-2,4,6-triiodo-1,3-benzenedicarboxamide

EXAMPLE 7a

N,N'-Bis[2-(acetyloxy)-1-[(acetyloxy)methyl]ethyl]-5-[[(2-propenyloxy)acetyl]amino]-2,4,6-triiodo-1,3-benzene-dicarboxamide Allyloxyacetyl chloride (9.0 g, 67 mmol) was added dropwise to a stirred solution of N,N'-bis[2-(acetyloxy)-1-

[(acetyloxy)methyl]ethyl]-5 -amino-2,4,6-triiodo-1,3-benzenedicarboxamide (30.0 g, 34 mmol) in N,N-dimethylacetamide (70 ml) at 0°–5° C. The reaction mixture was stirred at 5° C for 30 minutes and at room temperature for 20 hours. It was then slowly added dropwise to a well stirred mixture of ice-water (1.5 L), when a white solid separated out. This was collected by filtration, washed with water, and dried in vacuo to obtain N,N'-Bis[2-(acetyloxy)-1-[(acetyloxy)methyl]ethyl]-5-[(2-propenyloxy)acetyl]amino-2,4,6-triiodo-1,3-benzenedicarboxamide as a white amorphous solid (32.1 g, 97% yield), m.p. 214°–16°.

EXAMPLE 7b

N,N'-Bis[2-(acetyloxy)-1-[(acetyloxy)methyl]-2,4,6-triiodo-5-[3-(iodomethyl)-5-oxo-4-morpholinyl]-1,3-benzenedicarboxamide To a solution of N,N'-bis[2-(acetyloxy)-1-[(acetyloxy)methyl]ethyl]-2,4,6-triiodo-5-[(2-propenyloxy)acetyl ]amino-2,4,6-triiodo-1,3-benzenedicarboxamide of example 7a (1.95 g, 2 mmol) in dioxane (20 ml) and methanol (10 ml), was added aqueous sodium hydroxide (1 M) 15 ml, 15 mmol). After stirring for 2 hours, N-iodosuccinimide (0.45 g, 2 mmol) was added in portions over a 1 hour period. After 2 hours, more N-iodosuccinimide (0.45 g, 2 mmol) was added in portions to the clear yellow solution, and the stirring continued for 40 hours. The pH of the solution was adjusted to 7 and the solvent removed in vacuo at 40° C. A solution of the residue, thus obtained, in a mixture of pyridine (10 ml) and acetonitrile (5 ml) was treated with acetic anhydride (10 ml) and the reaction mixture stirred for 24 hours at room temperature. The solvents were completely removed in vacuo and the brown residue, upon chromatography over silica gel furnished pure N,N'-Bis[2-(acetyloxy)-1-[(acetyloxy)methyl]ethyl]-2,4,6-triiodo-5-[3-(iodomethyl)-5-oxo-4-morpholinyl]-1,3-benzene-dicarboxamide as a white fluffy solid (1.38 g, 63% yield).

EXAMPLE 7c

N,N'-Bis[2-(acetyloxy)-1-[(acetyloxy)methyl]ethyl]-5-[3-[(acetyloxy)methyl]-5-oxo-4-morpholinyl]-2,4,6-triiodo-1,3-benzenedicarboxamide To a solution of N,N'-Bis[2-(acetyloxy)-1-[(acetyloxy)methyl]ethyl]-2,4,6-triiodo-5-[3-(iodomethyl)-5-oxo-4-morpholinyl]-1,3-benzenedicarboxamide of example 7b (2.01 g, 1.83 mmol) in glacial acetic acid (35 ml), was added silver acetate (0.67 g, 4 mmol) and the mixture refluxed for 14 hours. The solvent was removed in vacuo at 40°, and the residue extracted with ethyl acetate (200 ml). The organic extract, after washing with saturated aqueous sodium bicarbonate (3×25 ml) and water (3×25 ml), was dried over anhydrous sodium sulfate. Removal of the solvent followed by purification of the crude product by column chromatography over silica gel, yielded analytically pure N,N'-Bis[2-(acetyloxy)-1-[(acetyloxy)methyl]ethyl]-5-[3[(acetyloxy)methyl]-5-oxo-4-morpholinyl]-2,4,6-triiodo-1,3-benzenedicarboxamide as a white fluffy solid (1.5 g, 82% yield), m.p. 208°–210°.

EXAMPLE 7d

N,N'-Bis[2-Hydroxy-1-(hydroxymethyl)ethyl]-5-[3-(hydroxymethyl)-5-oxo-4-morpholinyl]-2,4,6-triiodo-1,3-benzenedicarboxamide N,N'-Bis[2-(acetyloxy)-1-[(acetyloxy)methyl]ethyl]-5-[3-[(acetyloxy)methyl]-5-oxo-4-morpholinyl]-2,4,6-triiodo-1,3-benzenedicarboxamide of example 7c (1.03 g, 1 mmol) was added to a solution of sodium methoxide in methanol, prepared from sodium (23 mg, 1 mmol) and anhydrous methanol (20 ml). The solution was stirred for 4 hours at room temperature. The pH of the solution was then adjusted to 7 by the addition of Dowex-50 (H$^+$) resin. The resin was filtered off and the solvent removed from the filtrate to obtain a white solid (0.8 g) which, upon purification by low pressure reverse phase column chromatography over the CHP-20P resin yielded pure N,N'-Bis[2-Hydroxy-1-(hydroxymethyl)ethyl]-5-[3-(hydroxymethyl) -5-oxo-morpholinyl]-2,4,6-triiodo-1,3-benzenedicarboxamide as a snow-white glassy solid (0.65 g, 79% yield) .

EXAMPLE 8

N,N'-Bis[2,3-dihydroxypropyl]-5-(3-hydroxy-2-oxo-1-piperidinyl)-2,4,6-triiodo-1,3-benzenedicarboxamide

EXAMPLE 8a

N,N'-Bis[2,3-bis(acetyloxy)propyl]-5-[(2,5-dibromo-1-oxopentyl)amino]-2,4,6-triiodo-1,3-benzenedicarboxamide To a mixture of γ-valerolactone (20 g, 18.5 ml, 0.2 mol) and red phosphorus (2.31 g, 74.6 mmol) was added at 0° C. bromine (10.8 ml, 0.21 mol) dropwise with stirring over a half hour period in an atmosphere of nitrogen. The bath temperature was raised to 70° and more bromine (10.8 ml, 0.21 mol) was added dropwise over a half hour period. The solution was then heated at 80° C. for 3.0 hours. Dry nitrogen gas was bubbled into the cooled reaction mixture for one hour to remove the hydrogen bromide generated and the excess of bromine. The light red reaction mixture was distilled under reduced pressure (74°–78°, 0.15mm Hg) to obtain the crude product as a slightly colored oil (43.8 g). Fractional distillation of the crude product, furnished pure 2,5-dibromopentanoyl bromide as a colorless oil (35.3 g, yield 55%), b.p. 64°–66°/0.1 mm/Hg.

2,5-Dibromopentanoyl bromide (11 g, 34 mmol) was added dropwise to a stirred solution of N,N'-bis[2,3-bis(acetyloxy)propyl]-5-amino-2,4,6-triiodo-1,3-benzenedicarboxamide (23.0 g, 26.3 mmol) in N,N-dimethylacetamide (240 ml) at 0°. After the addition, the reaction mixture was stirred at 0° for 1 hour, and then at room temperature for 20 hours. The solvent was removed in vacuo at 45° and the resulting solid was dissolved in ethyl acetate (400 ml). The organic layer was washed with saturated aqueous sodium bicarbonate (1×70 ml), water (1×70 ml) and saturated sodium chloride (1×70 ml). After drying over magnesium sulfate, the solvent was removed in vacuo to obtain a yellow residue (28 g). Purification by column chromatography over silica gel furnished pure N,N'-bis[2,3-bis(acetyloxy)propyl] -5-[(2,5-dibromo-1-oxopentyl)amino]-2,4,6-triiodo-1,3-benzenedicarboxamide as an off-white crystalline compound (20.2 g, yield 69%).

EXAMPLE 8b

N,N'-Bis[2,3-bis(acetyloxy)propyl]-5-(3-bromo-2-oxo-1-piperidinyl]-2,4,6-triiodo-1,3-benzenedicarboxamide To a solution of N,N'-bis[2,3-bis(acetyloxy)propyl]-5-[(2, 5-dibromo-1-oxopentyl)amino]-2,4,6-triiodo-1,3-benzenedicarboxamide of example 8a (20.7 g, 18.5 mmol) in N,N-dimethylacetamide (200 ml), was added powdered potassium carbonate (20 g, 92 mmol) and the mixture was stirred at room temperature for 5 hours. The resulting slurry was filtered and the filtrate freed of the solvent to obtain a light brown solid, which was redissolved in ethyl acetate (500 ml). The solution was washed with water (2×50 ml) and saturated aqueous sodium chloride (1×100 ml) and then dried over magnesium sulfate. The solvent was removed in vacuo and the crude product (18.1 g) purified by column chromatography over silica gel to obtain pure N,N'-bis[2,3-bis(acetyloxy)propyl]-5-(3-bromo-2-oxo-1-piperidinyl]-2,4,6-triiodo-1,3-benzenedicarboxamide as a white solid (14.04 g, 80% yield), m.p. 232°–35°.

EXAMPLE 8c

5-[3-(Acetyloxy)-2-oxo-1-piperidinyl]N,N'-bis[2,3-bis(acetyloxy)propyl]-2,4,6-triiodo-1,3-benzenedicarboxamide To a solution of N,N'-bis[2,3-bis(acetyloxy)propyl]-5-(3-bromo-2-oxo-1-piperidinyl)-2,4,6-triiodo-1,3-benzenedicarboxamide of example 8b (13.7 g, 13.3 mmol) in glacial acetic acid (400 ml), was added silver acetate (5.6 g, 33.5 mmol) and the mixture was refluxed for 21 hours. After cooling to room temperature, the mixture was filtered, and the filtrate concentrated in vacuo. The residue thus obtained, was redissolved in ethyl acetate (500 ml) and washed successively with water (50 ml), saturated aqueous sodium bicarbonate (3×50 ml) and saturated aqueous sodium chloride (50 ml). After drying over magnesium sulfate, the solvent was evaporated in vacuo and the crude product, that resulted, was purified by column chromatography over silica gel to obtain 5-[3-(acetyloxy)-2-oxo-1-piperidinyl]-N,N'-bis[2,3-bis(acetyloxy)propyl]-2,4,6-triiodo-1,3-benzenedicarboxamide as a white fluffy solid (10.3 g, 83% yield).

EXAMPLE 8d

N,N'-Bis[2,3-dihydroxypropyl]-5-(3-hydroxy-2-oxo-1-piperidinyl]-2,4,6-triiodo-1,3-benzenedicarboxamide A solution of 5-[3-(acetyloxy)-2-oxo-1-piperidinyl]-N,N'-bis[2,3-bis(acetyloxy)propyl]-2,4,6-triiodo-1,3-benzenedicarboxamide of example 8c (4 g, 4.3 mmol) in methanol (20 ml) was treated with a solution of sodium methoxide in methanol, prepared from sodium (30 mg, 1.3 mmol) and anhydrous methanol (20 ml), and the mixture was stirred at room temperature for 2 hours. The pH of the solution was adjusted down to 7 by the addition of Dowex-50 (H$^+$) resin. The mixture was filtered and the filtrate was freed of the solvent to obtain the crude product. Purification by low pressure reverse phase column chromatography over the CHP-20P resin furnished analytically pure N,N'-Bis[2,3-dihydroxypropyl]-5-(3-hydroxy-2-oxo-1-piperidinyl)-2,4,6-triiodo-1,3-benzenedicarboxamide as a snow-white glassy solid (2.3 g, 78% yield).

EXAMPLE 9

N,N'-Bis[2-hydroxy-1-(hydroxymethyl)ethyl]-5-(3-hydroxy-2-oxo-1-piperidinyl]-2,4,6-triiodo-1,3-benzenedicarboxamide

EXAMPLE 9 a

N,N'-Bis[2-(acetyloxy)-1-[(acetyloxy)methyl]ethyl]-5-[(2,5-dibromo-1-oxopentyl)amino]-2,4,6-triiodo-1,3-benzenedicarboxamide 2,5-Dibromopentanoyl bromide prepared as described in example 8a (15.9 g, 49.3 mmol) was added dropwise to a stirred solution of N,N'-bis[2-(acetyloxy)-1-[(acetyloxy)methyl]ethyl]-5-amino-2,4,6-triiodo-1,3-benzenedicarboxamide (33 g, 37.8 mmol) in dimethylacetamide (250 ml) at 0°. After the addition, the reaction mixture was stirred at 0° for 1 hour, and then at room temperature for 22 hours. The solution was then added slowly dropwise to a well stirred mixture of ice-water (2 L), when a white solid separated out. This was collected by filtration, washed with ice-water (3×50 ml), and dried in vacuo to obtain the crude product (40.1 g, 91.5% pure). Recrystallization from ethyl acetate furnished analytically pure N,N'-bis[2-(acetyloxy)-1-[(acetyloxy)methyl]ethyl]-5-[(2,5-dibromo-1-oxopentyl)amino]-2,4,6-triiodo-1,3-benzenedicarboxamide as an off-white crystalline compound (35.3 g, 84% yield), m.p. 240°–243°.

EXAMPLE 9b

N,N'-Bis[2-(acetyloxy)-1-[(acetyloxy)methyl]ethyl]-5-(3-bromo-2-oxo-1-piperidinyl]-2,4,6-triiodo-1,3-benzenedicarboxamide To a solution of N,N'-bis[2-(acetyloxy)-1-[(acetyloxy)methyl]ethyl]-5-[(2,5-dibromo-1-oxopentyl)amino]-2,4,6-triiodo-1,3-benzenedicarboxamide of example 9a (32.5 g, 29.1 mmol) in dimethylacetamide (250 ml), was added powdered potassium carbonate (25.2 g, 116.5 mmol). After stirring for 4 hours, the mixture was filtered. The filtrate was freed of the solvent in vacuo at 45° C. and the resulting solid was redissolved in ethyl acetate (500 ml). The ethyl acetate solution was washed with water (2×50 ml) and saturated aqueous sodium chloride (1×100 ml), and dried over anhydrous magnesium sulfate. The solvent was removed in vacuo to obtain a white solid (29.5 g) which, upon crystallization from ethyl acetate (1.2 L), furnished analytically pure N,N'-bis[2-acetyloxy)-1-[(acetyloxy) -methyl]ethyl]-5-(3-bromo-2-oxo-1-piperidinyl)-2,4,6-triiodo-1,3-benzenedicarboxamide as a white crystalline solid (23.95 g, 79.5% yield), m.p. 231°–3°.

EXAMPLE 9c

N,N'-Bis[2-(acetyloxy)-1-[(acetyloxy)methyl]ethyl]-5-[3-(acetyloxy)-2-oxo-1-piperidinyl]-2,4,6-triiodo-1,3 -benzene-dicarboxamide A mixture of N,N'-bis[2-(acetyloxy)-1-[(acetyloxy)methyl]ethyl]-5-[3-bromo-2-oxo-1-piperidinyl]-2,4,6-triiodo-1,3-benzenedicarboxamide of example 9b (22.43 g, 21.67 mmol) and silver acetate (12.5 g, 74.8 mmol) in glacial acetic acid (400 ml) was refluxed for 28 hours. The reaction mixture was cooled to room temperature and then filtered. The filtrate was freed of the solvent in vacuo at 45° and the resulting residue was dissolved in ethyl acetate (500 ml). The ethyl acetate solution was washed successively with water (2×50 ml), saturated aqueous sodium bicarbonate (2×50 ml) and saturated aqueous sodium chloride (2×50 ml), and then dried over anhydrous magnesium sulfate. Removal of the solvent yielded a white powder (20.7 g), which upon crystallization from ethyl acetate (1.1 L), furnished analytically pure N,N'-bis [2-(acetyloxy)-1-[(acetyloxy)methyl]ethyl]-5-[3-(acetyloxy)-2-oxo-1-piperidinyl]-2,4,6-triiodo-1,3-benzenedicarboxamide as a white fluffy solid (15.45 g, 70% yield).

EXAMPLE 9d

N,N'-Bis[2-hydroxy-1-(hydroxymethyl)ethyl]-5-(3-hydroxy-2-oxo-1-piperidinyl]-2,4,6-triiodo-1,3benzenedicarboxamide A solution of N,N'-bis[2-acetyloxy)-1-[(acetyloxy)methyl]ethyl]-5-(3-hydroxy-2-oxo-1-piperidinyl)-2,4,6-triiodo-1,3-benzenedicarboxamide of example 9c (2.0 g, 2.16 mmol) in methanol (10 ml) was treated with a solution of sodium methoxide in methanol, prepared from sodium (23 mg, 1 mmol) and anhydrous methanol (10 ml). The reaction mixture was stirred at room temperature for 3 hours. The pH of the solution was then adjusted to 7 by adding Dowex-50 (H+) resin. The resin was filtered off and the filtrate was freed of the solvent in vacuo to obtain the crude product as a color less glass (1.47 g). Purification by low pressure reverse phase column chromatography over the CHP-20P resin afforded analytically pure N,N'-Bis[2-hydroxy-1-(hydroxymethyl)ethyl]-5-(3-hydroxy-2-oxo-1-piperidinyl]-2,4,6-triiodo-1,3-benzenedicarboxamide as a snow-white glassy solid (1.0 g, 68% yield).

EXAMPLE 10

N,N'-Bis-[2,3-dihydroxy-1-propyl]-5-2-oxo-1-pyrrolidinyl]-2,4,6-triiodo-1,3-benzenedicarboxamide

EXAMPLE 10a

N,N'-Bis-[2,3-bis-(acetyloxy)-1-propyl]-5-[4-chloro-1-oxobutyl]-2,4,6-triiodo-1,3-benzenedicarboxamide To a solution of N,N'-bis-[2,3-bis-(acetyloxy)-1-propyl]-5-amino-2,4,6-triiodo-1,3-benzenedicarboxamide (87.3 grams, 100 mmol) in dry N,N-dimethylacetamide (370 ml) was added 4-chlorobutyryl chloride (20.9 g, 148 mmol) via a syringe over a period of 2 minutes under $N_2$. The mixture was stirred for 68 hours at ambient temperature. The entire reaction mixture was poured into ice-water (800 ml) containing sodium bicarbonate (20 g). The anilide precipitated as a tacky mass and the mixture was extracted with ethyl acetate (100 ml). The organic layer was removed and the aqueous layer was washed with ethyl acetate (2×300 ml). The organic layers were combined, washed with an equal volume of saturated aqueous sodium chloride solution in two batches and dried (magnesium sulfate). The solvents were removed and the resulting crude product was dried overnight at high vacuum to give an almost immobile orange syrup (114.5 g). Recrystallization of the crude product from ethylacetate/hexanes gave N,N'-bis-[2,3-bis-(acetyloxy)-1-propyl]-5-[4-chloro-1-oxobutyl]-2,4,6-triiodo-1,3-benzenedicarboxamide as an off-white powder (82.5 g, 84% yield), m.p. (211°–214°).

EXAMPLE 10b

N,N'-Bis-[2,3-bis-(acetyloxy)-1-propyl]-5-[2-oxo-1-pyrrolidinyl]-2,4,6-triiodo-1,3-benzenedicarboxamide A solution of N,N'-bis-[2,3-bis-(acetyloxy)-1-propyl]-5-[4-chloro-1-oxobutyl]-2,4,6-triiodo-1,3-benzenedicarboxamide (55.36 g, 56.6 mmol) in N,N'-dimethylacetamide (500 ml) was cooled to −16.5° under $N_2$ and finely powdered potassium carbonate (54.76 g, 396.3 mmol) was added over a period of 2 minutes. The mixture was stirred for 44 hours at −16.5°. The heterogeneous reaction mixture that resulted was filtered under vacuum. The volatiles were evaporated from the filtrate under high vacuum at a bath temperature of 40°–45°; near the end of the evaporation the bath temperature was raised to 50° C. The resulting thick, glassy syrup was dissolved in ethyl acetate (350 ml) and the solution was washed with an equal volume of distilled water. The layers were separated and the ethyl acetate layer was washed with water (350 ml) and then with saturated aqueous sodium chloride solution (350 ml). The organic layer was set aside and the first aqueous extract was backextracted with ethyl acetate (300 ml). The resulting organic layer was washed with water (2×200 ml) and saturated aqueous sodium chloride solution (2×150 ml). The organic layers were combined and dried over magnesium sulfate and the solvents were removed. The crude product thus obtained was purified by flash chromatography over silica gel using ethyl acetate/dichloromethane 2/1, followed by ethyl acetate/dichloromethane 4/1, eluent. This gave N,N'-Bis-[2,3-bis-(acetyloxy)-1-propyl]-5-[2-oxo-1pyrrolidinyl]-2,4,6-triiodo-1,3-benzenedicarboxamide (32.24 g, 60.5% yield) as an off-white foam. A sample, crystallized for analysis from ethyl acetate/hexanes, had m.p. 130°–133°.

EXAMPLE 10c

N,N'-Bis-[2,3-dihydroxy-1-propyl]-5-[2-oxo-1-pyrrolidinyl]-2,4,6-triiodo-1,3-benzenedicarboxamide N,N'-bis-[2,3-bis-(acetyloxy)-1-propyl]-5-[2-oxo-1-pyrrolidinyl]-2,4,6-triiodo-1,3-benzenedicarboxamide (24.88 g, 26.64 mmol) was dissolved in Mg°-dried methanol (200 ml) under $N_2$. To this solution was added a solution of sodium methoxide in methanol, prepared by dissolving sodium (0.158 g, 6.52 mmol) in Mg°-dried methanol (10 ml) at 0° under $N_2$ with stirring. The reaction mixture was stirred at ambient temperature for 7 hours.

BioRad Dowex AG-50 X8 resin (H+ form) (30 g) was added to the reaction mixture and the mixture was stirred for 20 minutes. The pH was adjusted to 4.4 by the addition of 4 drops of glacial acetic acid. The resin was removed by filtration and was rinsed with several 50 ml portions of methanol. The volatiles were removed and the residue was further dried under a vacuum of 0.5 mm of Hg overnight. The crude foam obtained was dissolved in distilled, deionized water and applied to a column of CHP-20 resin. The compound was eluted with 5.5%–12% aqueous ethanol. The eluate was evaporated to give N,N'-bis-[2,3-dihydroxy-1-propyl]-5-[2-oxo-1-pyrrolidinyl]-2,4,6- triiodo-1,3-benzenedicarboxamide (13.87 g, 67.3% yield) as a white foam. A sample, crystallized for analysis from isopropanol, afforded the product as a white powder, (m.p. >265°).

EXAMPLE 11

N,N'-Bis-[2-(hydroxy)-1-(hydroxymethyl)ethyl-5-[2-(hydroxymethyl)]-5-oxo-1-pyrrolidinyl]-2,4,6-triiodo-1,3-benzenedicarboxamide

EXAMPLE 11a

N,N'-Bis[2-(acetyloxy)-1-[(acetyloxy)methyl]ethyl]-2,4,6-triiodo-5-[(1-oxo-4-pentenoyl)amino]-1,3-benzenedicarboxamide 4-Pentenoyl chloride (11.9 g, 100 mmol) was added to a stirred solution of N,N'-bis[2-(acetyloxy)-1-[(acetyloxy)methyl]ethyl]-5-amino-2,4,6-triiodo-1,3-benzenedicarboxamide (47.75 g, 50 mmol) in dimethylacetamide (400 ml) at room temperature and the mixture was stirred for 16 hours. Dimethylacetamide was removed in vacuo and the residue dissolved in ethyl acetate (600 ml). The solution was washed with aqueous sodium bicarbonate (10%, 2×150 ml), water (2×100 ml), and brine (150 ml). The organic layer was dried and the solvent removed to obtain the crude product as an off-white solid. Purification by crystallization from a mixture of acetone (250 ml) and hexane (75 ml) afforded N,N'-bis[2-(acetyloxy)-1-[(acetyloxy)methyl]ethyl]-2,4,6-triiodo-5-[(1-oxo-4-pentenoyl)amino]-1,3-benzenedicarboxamide (42.5 g, yield, 81%).

EXAMPLE 11b

N,N'-Bis[2-(acetyloxy)-1-[(acetyloxy)methyl]ethyl]-5-[2-(iodomethyl)-5-oxo-1-pyrrolidinyl]-2,4,6-triiodo-1,3-benzenedicarboxamide To a solution of N,N'-bis[2-(acetyloxy)-1-[(acetyloxy)methyl]ethyl]-2,4,6-triiodo-5-[(1-oxo-4-pentenoyl)amino]-1,3-benzenedicarboxamide (19.1 g, 20 mmol) in methanol (200 ml) was added a solution of sodium methoxide in methanol, prepared by dissolving sodium (1.38 g, 60 mmol) in methanol (30 ml). The mixture was stirred for 30 minutes. The solvent was removed in vacuo and the residue was dissolved in a mixture of methanol and water (1:1, v/v; 200 ml). N-Iodosuccinimide (12.32 g, 60 mmol) was added and the mixture stirred at room temperature for 48 hours. The solvents were removed from the reaction mixture and the residue azeotroped with ethanol (3×150 ml). The residue was then dissolved in pyridine (150 ml) and treated with acetic anhydride ((20.4 g, 200 mmol) with stirring for 17 hours at room temperature. The excess of pyridine and acetic anhydride were removed in vacuo, the residue dissolved in ethyl acette (500 ml), and the resulting solution washed successively with water (200 ml), aqueous sodium thiosulfate (25%, 2×125 ml), and water (2×150 ml). The organic layer was dried and removal of the solvent afforded the product as a light yellow glassy solid (20.2 g). The crude product was purified by column chromatography over silica gel, using 25% hexane in ethyl acetate as the eluent, to obtain N,N'-bis[2-(acetyloxy)-1-[(acetyloxy)methyl]ethyl]-5-[2-(iodomethyl)-5-oxo-1-pyrrolidinyl]-2,4,6-triiodo-1,3-benzenedicarboxamide (13.2 g, 61.2%) as a colorless powder.

EXAMPLE 11c

N,N-Bis[2-(acetyloxy)-1-[(acetyloxy)methyl]ethyl]-5-[2-(acetyloxy)methyl)-5-oxo-1-pyrrolidinyl]-2,4,6-triiodo-1,3-benzenedicarboxamide To a solution of N,N'-bis[2-(acetyloxy)-1-(acetyloxy)methyl]ethyl]-5-[2-(iodomethyl)-5-oxo-1-pyrrolidinyl]-2,4,6-triiodo-1,3-benzenedicarboxamide (12.00 g, 110 mmol) in acetonitrile (150 ml) was added tetraethylammonium acetate (5.74 g, 22 mmol) and the mixture stirred at 50° for 18 hours. Acetonitrile was removed in vacuo at 60°, the residue dissolved in ethyl acetate (200 ml), and the resulting solution washed with brine (2×100 ml) and with water (100 ml). The ethyl acetate layer was dried and removal of the solvent afforded the crude product as a colorless glassy solid. This material was purified by column chromatography over silica gel, using 20% hexane in ethyl acetate as eluent, to obtain N,N-bis[2-(acetyloxy)-1-[(acetyloxy)methyl]ethyl]-5-[2-(acetyloxy)methyl)-5-oxo-1-pyrrolidinyl]-2,4,6-triiodo-1,3-benzenedicarboxamide as a colorless solid (9.4 g, 83.6% yield).

EXAMPLE 11d

N,N'-Bis-[2-(hydroxy)-1-(hydroxymethyl)ethyl]-5-[2-(hydroxymethyl)]-5-oxo-1-pyrrolidinyl]-2,4,6-triiodo-1,3-benzenedicarboxamide A solution of N,N-bis[2-(acetyloxy)-1-[(acetyloxy)methyl]ethyl]-5-[2-(acetyloxy)methyl)-5-oxo-1-pyrrolidinyl]-2,4,6-triiodo-1,3-benzenedicarboxamide (8.4 g, 8.3 mmol) in methanol (50 ml) was treated with a solution of sodium methoxide in methanol, prepared from sodium (190 mg, 8.3 mmol) and methanol (5 ml). The solution was stirred at room temperature for 1 hour. The pH of the solution was then adjusted to 7 with the ion exchange resin Dowex-50-(H)$^+$. The resin was filtered off and the solvent removed to obtain the crude product as a glassy solid (6.45 g, 96.8%). This product was purified by reverse phase column chromatography using the nonionic CHP-20 resin and a solvent gradient varying from 100% deionized water to water containing 4% ethanol. The fractions containing the pure compound were combined and the solvents removed to obtain N,N'-Bis-[2-(hydroxy)-1-(hydroxymethyl)ethyl]-5-[2-(hydroxymethyl)]-5-oxo-1-pyrrolidinyl]-2,4,6-triiodo-1,3-benzenedicarboxamide as a colorless solid (5.88 g, yield 88%). M.P. 245°–248° C.

EXAMPLE 12

N,N'-Bis(2,3-Dihydroxypropyl)-5-[3-(hydroxymethyl)-5-oxo-4-morpholinyl]-2,4,6-triiodo-1,3-benzenedicarboxamide EXAMPLE 12a N,N'-Bis[2,3-bis(acetyloxy)propyl]-2,4-6-triiodo-5-[((2-propenyloxy)acetyl)amino]-1,3-benzenedicarboxamide Allyloxyacetyl chloride (4.0 gm, 30 mmol) was added dropwise to a stirred solution of N,N'-bis[2,3-bis(acetyloxy)propyl]-5-amino-2,4,6-triiodo-1,3-benzenedicarboxamide (22.69 g, 26 mmol) in dimethylacetamide (100 ml) at 0°–5°. The reaction mixture was stirred at 5° for 30 minutes and at room temperature for 20 hours. It was then added dropwise to a well stirred mixture of ice-water (1L), when a gummy solid separated out. This was collected be decantation and dissolved in ethyl acetate (200 ml). The aqueous layer was extracted with ethyl acetate (2×200 ml). The combined organic layers were washed with water (2×100 ml), dried (MgSO$_4$), and concentrated to obtain a foamy solid (24.8 g). Purification by column chromatography over silica gel using a gradient system of ethyl acetate/hexane (1:3–3:1) furnished N,N'-bis[2,3-bis(acetyloxy)propyl]-2,4-6-triiodo-5-[((2-propenyloxy)acetyl)amino]-1,3-benzenedicarboxamide as a white foamy solid 19.84 g, 77% yield).

EXAMPLE 12b

N,N'-Bis[2,3-bis(acetyloxy)propyl]-2,4,6-triiodo-5-[3-iodomethyl)-5-oxo-4-morpholinyl]-1,3-benzenedicarboxamide To a solution of N,N'-Bis[2,3-bis(acetyloxy)propyl]-2,4,6-triiodo-5-[3-iodomethyl)-5-oxo-4-morpholinyl]-1,3-benzenedicarboxamide (10.7 g, 11 mmol) in anhydrous methanol (100 ml), was added a solution of sodium methoxide in methanol, prepared by dissolving sodium metal (25 mg) in dry methanol (5 ml). After stirring for 4 hours, the solvent was removed and the residue was redissolved in a mixture of dioxane-methanol (150 ml, 1:3). An aqueous solution of sodium hydroxide (1M, 30 ml) was added, and the mixture stirred for 2 hours. N-Iodosuccinimide (3.38 g, 15 mmol) was then added in portions over a 2 hour period. After stirring further for 2 hours, more N-iodosuccinimide (2.25 g, 10 mmol) was added in portions to the clear yellow solution and the stirring continued for 40 hours. The pH of the solution was adjusted to 7 and the solvent removed in vacuo at 40°. The residue was stirred in a mixture of pyridine (25 ml, acetic anhydride (25 ml) and acetonitrile (20 ml) for 24 hours. The solvents were removed in vacuo and the brown residue, upon column chromatography over silica gel using a stepwise gradient of ethyl acetate-hexane (from 1:2 to 9:1), afforded pure N,N'-bis[2,3-bis(acetyloxy)propyl]-2,4,6-triiodo-5-[3-iodomethyl)5-oxo-4-morpholinyl]-1,3-benzenedicarboxamide (7.5 g, 62% yield) as a white amorphous solid, m.p. 168°–70°.

EXAMPLE 12c

N,N'-Bis[2,3-bis(acetyloxy)propyl]-5-[3-((Acetyloxy)methyl]-5-oxo-4-morpholinyl]-2,4,6-triiodo-1,3-benzenedicarboxamide To a solution of N,N'-bis[2,3-bis(acetyloxy)propyl]-5-[3-iodomethyl)-5-oxo-4-morpholinyl]-1,3-benzenedicarboxamide (7.8 g, 7.1 mmol) in acetic acid (100 ml) was added silver acetate (4.0 g, 24 mmol). The mixture was stirred and refluxed for 24 hours. The mixture was then filtered to remove inorganic salts, which were washed with acetic acid (50 ml), followed by ethyl acetate (100 ml). The combined filtrate and washings were concentrated to dryness. The resulting residue was redissolved in ethyl acetate (200 ml). The ethyl acetate solution was washed successively with water (3×50 ml), saturated aqueous sodium bicarbonate (3×50 ml) and water (3×50 ml). Drying over anhydrous sodium sulfate, followed by removal of the solvent under reduced pressure, yielded the crude product as a light brown solid (7.2 g). Purification by column chromatography over silica gel using a gradient system of ethyl acetate/hexane as eluent afforded N,N'-bis[2,3-bis(acetyloxy)propyl]-5-[3-(Acetyloxy)methyl-5-oxo-4-morpholinyl]-2,4,6-triiodo-1,3-benzenedicarboxamide as an amorphous solid (5.36 g, 73% yield), m.p. 210°–212°.

EXAMPLE 12d

N,N'-Bis(2,3-dihydroxypropyl)-5-[3-(hydroxymethyl)-5-oxo-4-morpholinyl]-2,4,6-triiodo-1,3-benzenedicarboxamide To a solution of N,N'-bis[2,3-bis(acetyloxy)propyl]-5-[3-(Acetyloxy)methyl-5-oxo-4-morpholinyl]-2,4,6-triiodo-1,3-benzenedicarboxamide (5.15 g, 5 mmol) in anhydroous methanol (100 ml), was added a solution of sodium methoxide, prepared from sodium (25 mg) and anhydrous methanol (5 ml), and the mixture was stirred for 3 hours. The solution was adjusted to pH 7 by a slow addition of Dowex-50 (H+) resin and then filtered. The filtrate was concentrated in vacuo to obtain the crude product (3.85 g) as a white solid. The material was dissolved in water (40 ml) and loaded onto a column of CHP-20 diaion resin. The column was first eluted with water (1L) and then with a stepwise gradient of ethanol in water (1–8%). The fractions containing the pure product were combined and the solvents removed in vacuo to obtain N,N'-Bis(2,3-dihydroxypropyl)-5-[3-(hydroxymethyl)-5-oxo-4-morpholinyl]-2,4,6-triiodo-1,3-benzenedicarboxamide as a white microcrystalline solid (2.45 g, 60% yield, 99% purity). Recrystallization from ethanol/isopropanol (95/5) afforded the analytical sample as a white solid, m.p. 227°–230°.

EXAMPLE 13

N,N'-Bis(2,3-Dihydroxypropyl)-5-(2-oxo-1-piperidinyl)-2,4,6-triiodo-1,3-benzenedicarboxamide

EXAMPLE 13a

N,N'-Bis[2,3-bis(Acetyloxy)propyl]-5-[(5-chloro-1-oxo-pentyl)amino]-2,4,6-triiodo-1,3-benzenedicarboxamide 5-Chloropentanoyl chloride (5.1 g, 33 mmol) was added dropwise to a stirred solution of N,N'-bis[2,3-bis(acetyloxy)propyl]-5-amino-2,4,6-triiodo-1,3-benzenedicarboxamide (20.5 g, 23 mmol) in N,N'-dimethylacetamide (75 ml) at 0°–5°. The reaction mixture was stirred at 5° for 1 hour, and then at room temperature for 30 hours. The solvent was removed in vacuo and the residue was dissolved in ethyl acetate (250 ml). The solution was washed with water (2×50 ml), followed by saturated aqueous NaCl (50 ml), and then dried over anhydrous sodium sulfate. Removal of the solvent in vacuo gave N,N'-bis[2,3-bis(acetyloxy)propyl]-5-[(5-chloro-1oxopentyl)amino]-2,4,6-triiodo-1,3-benzenedicarboxamide as an off-white fluffy solid (22.1 g, yield 97%, purity 98.5%).

EXAMPLE 13b

N,N'-bis[2,3-bis(acetyloxy)propyl]-5-(2-oxo-1-piperidinyl)-2,4,6-triiodo-1,3-benzenedicarboxamide To a solution of N,N'-bis(acetyloxy)propyl]-5-[(5-chloro-1-oxopentyl)amino]-2,4,6-triiodo-1,3-benzenedicarboxamide (23,8 g, 24 mmol) in dimethyl acetamide (200 ml) was added powdered anhydrous potassium carbonate (16.5 g, 120 mmol) and the mixture stirred for 4 hours at room temperature. The reaction mixture was filtered and the filtrate concentrated in vacuo to obtain a brown fluffy solid (23 g, purity 96.7%, crude yield 99%). Purification of this material by column chromatography over silica gel afforded pure N,N'-bis[2,3-bis(acetyloxy)propyl]-5-(2-oxo-1-piperidinyl)-2,4,6-triiodo-1,3-benzenedicarboxamide as white fluffy solid (20.1 g, purity 99%, yield 87%, m.p. 130°–134° (white needles from acetone/hexane).

EXAMPLE 13c

N,N-bis(2,3-Dihydroxypropyl)-5-(2-oxo-1-piperidinyl)-2,4,6-triiodo-1,3-benzenedicarboxamide To a solution of N,N'-bis[2,3-bis(acetyloxy)propyl]-5-(2-oxo-1-piperidinyl)-2,4,6-triiodo-1,3-benzenedicarboxamide (17.2 g, 18 mmol) in anhydrous methanol (100 ml) was added a solution of sodium methoxide, prepared by dissolving 48 mg of sodium in 2 ml of methanol. The mixture was stirred for 4 hours and the pH of the solution adjusted to 7 by the addition of AG 50W-X8 (H+ form). The resin was filtered off and the filtrate decolorized by treatment with activated charcoal and again filtered. The clear colorless filtrate, upon removal of the solvent, gave the crude product as a white solid (14.3 g, purity 99%), which was redissolved in water (100 ml) and purified by low pressure reverse phase column chromatography over the CHP-20 dianion resin. The fractions containing the pure product were combined and the solvents removed in vacuo to obtain N,N-bis(2,3-dihydroxypropyl)-5-(2-oxo-1-piperidinyl)-2,4,6-triiodo-1,3-benzenedicarboxamide as a white crystalline solid (11.95 g, yield 84.5%, purity 99.9%, m.p. 214°–219°.

EXAMPLE 14

N,N'-Bis(2,3-dihydroxypropyl)-5-(3,3-dimethyl-2-oxo-1-azetidinyl)-2,4,6-triiodo-1,3-benzenedicarboxamide A. N,N'-Bis-[2,3-diacetyloxy-1-propyl]-5-[3-chloro-2,2-dimethyl-1-oxo-propyl]-amino-2,4-6-triodo-1,3-benzenedicarboxamide To a solution of N,N'-bis[2,3-diacetyloxy-1-propyl]-5-amino-2,4,6-triodo-1,3-benzenedicarboxamide (10.0 g, 11.4 mmol, prepared as described in U.S. Pat. No. 4,396,598) in 25 ml of anhydrous dimethylacetamide, was added 3-chloropivaloyl chloride (10.6 g, 68.4 mmol), and the reaction mixture stirred at 60° C. for 70 hours. Dimethylacetamide was removed in vacuo. the residue was dissolved in ethyl acetate (400 ml), and the solution was washed with aqueous sodium hydrogen carbonate solution (100 ml) and with water until neutral. The organic layer was dried and the solvent removed to obtain the title A product as a light yellow glassy solid, which was further purified by flash chromatography using MeOH/CHCl$_3$ (0–5%). Fractions containing the pure product were combined and removal of the solvent afforded pure N,N'-bis[diacetyloxy-1-propyl]-5-[3-chloro-2,2-dimethyl-1-oxo-propyl]-amino-2,4,6-triodo-1,3-benzenedicarboxamide as a light yellow glassy solid (7.22 g).

Elemental analysis calc'd for $C_{27}H_{33}N_3ClI$. 0.78 $H_2O$: C, 32.24; H, 3.46; N, 4.18; Cl, 3.52; I, 37.85; 0, 18.74; Found: C, 32.61; H, 3.09; N, 3.81; Cl, 3.55; I, 38.15.

B. N,N'-bis-[2,3-diacetyloxy-1-propyl]-5-[3,3-dimethyl-2-oxo-1-azetidinyl]-2,4,6-triiodo-1,3-benzene-dicarboxamide To a solution of the title A compund (7.0 g, 7.1 mmol) in anhydrous dimethylacetamide (40 ml) was added anhydrous potassium carbonate (7.0 g, 50 mmol). The suspension was stirred at room temperature for 20 hours. Dimethylacetamide was removed in vacuo, the residue was dissolved in ethyl acetate (300 ml) and the solution was washed with water (3×100 ml). The organic layer was dried and the solvent removed to obtain the crude product as a light yellow glassy solid. Recrystallization of this product from ethyl acetate/hexane (5:1) afforded pure N,N'-bis-[2,3-diacetyloxy-1-propyl]-5-[3,3-dimethyl-2-oxo-1-azetidinyl]-2,4,6-triiodo-1,3-benzene-dicarboxamide as a white solid (5.6 g).

Elemental analysis calc'd for C27H32N3I3O11: C, 33.95; H, 3.38; N, 4.40; I, 39.85; O, 18.42; Found: C, 33.95; H, 3.51; N, 4.34; I, 40.00.

C. N,N'-bis-[2,3-dihydroxy-1-propyl]-5-[3,3-dimethyl-2-oxo-1-azetidinyl]2,4,6-triiodo-1,3-benzene-dicarboxamide To a solution of the title B compound (5.75 g, 6.02 mmol) in 20 ml of methanol was added NaOMe [prepared from Na (161 mg, 7 mmol) in methanol (5 ml)]. The mixture was stirred at room temperature for 1 hour. The solution was treated with Dowex 50 (H$^+$) and the solvent removed to obtain the crude product, which was purified on a CHP-20 column using ethyl alcohol/water (0–20%). Fractions containing the pure product were combined and removal of the solvent afforded pure N,N'-bis-[2,3-dihydroxy-1-propyl]-5-[3,3-dimethyl-2-oxo-1-azetidinyl]2,4,6-triiodo-1,3-benzene-dicarboxamide as a colorless glassy solid (4.3 g).

Analysis calc'd for $C_{19}H_{24}N_3I_3O_7$.0.92 $H_2O$: C, 28.40; H, 3.24; N, 5.23; I, 47.37; Found: C, 28.13; H, 3.05; N, 5.36; I, 47.06; $H_2O$, 2.06.

EXAMPLE 15

N,N'-Bis(2,3-dihydroxypropyl)-5-(hexahydro-3-hydroxy-2-oxo-1H-azepin-1-yl)-2,4,6-triiodo-benzenedicarboxamide A. 2,6-Dibromohexanoyl bromide ε-Caprolactone (6.0 g, 52.5 mmol) was added to red phosphorus (0.6 g, 19.9 mmol), the reaction vessel was cooled to 0°, and bromine (9.2 g, 57.5 mmol) was added dropwise with stirring over a half-hour period. The bath temperature was raised to 70° and more bromine (9.2 g, 57.5 mmol) was added dropwise over a half hour period. A sodium hydroxide trap was installed to remove the resulting hydrogen bromide and excess bromine gases formed. The reaction vessel was equipped with a drying tube to protect from moisture. After the addition of the bromine was complete, the solution was heated at 80° for 3.75 hours. The cooled reaction mixture was purged with dry nitrogen gas for about 1 hour to remove hydrogen bromide and bromine. The dark red reaction mixture was distilled under reduced pressure 128°–130°/0.75 mm Hg) to give the tribomide as a slightly colored liquid. This material was further purified by fractional redistillation to furnish pure title A 2,6-dibromohexanoyl bromide (5.20 g) (90°–92°/0.15 mm Hg) as a clear colorless liquid, bp 90°–92° (0.15 mm Hg).

Microanalysis calc'd for $C_6H_9Br_{3O}$: C, 21.39; H, 2.69; Br, 71.16; O, 4.75; Found: C, 21.76; H, 2.69; Br, 71.43.

B. N,N'-Bis[2,3-bis(acetyloxy)-1-propyl]-5-[(2,6-dibromo-1-oxo-hexyl)amino]-2,4,6-triiodo-1,3-benzenedicarboxamide The title A 2,6-dibromohexanoyl bromide (2.07 g, 6.10 mmol) was added dropwise to a stirred solution of N,N'-bis [2,3-bis(acetoxy)-1-propyl]-5-amino-2,4,6-triiodo-1,3-benzenedicarboxamide (prepared as described in U.S. Pat. No. 4,396,598) (3.98 g, 4.66 mmol) in dry N,N'-dimethylacetamide (DMA) (10 mL) at 0°. After the addition, the reaction mixture was stirred at 0°–5° for 1 hour, then at room temperature for 21 hours. Upon complete conversion of the starting material to product, the reaction was worked up by removal of solvent in vacuo at 40° followed by dissolving the resulting solid in ethyl acetate (200 mL). The organic layer was washed with water (1×60 mL), saturated aqueous sodium bicarbonate (1×60 mL) and saturated aqueous sodium chloride (60 mL). The organic extract was dried over anhydrous sodium sulfate, filtered and the solvent evaporated in vacuo to obtain the crude compound as a slightly yellow solid (5.1 g). This material was used as such in the next step. TLC: Rf 0.30 (silica gel, ethyl acetate/hexane 75:15)

Microanalysis calc'd for $C_{28}H_{34}N_3O_{11}I_3Br_2$: C, 29.79; H, 3.04; N, 3.72; Br, 14.15; I, 33.72; O, 15.59; Found: C, 29.81; H, 3.01; N, 3.40; Br, 14.03; I, 33.42.

C. N,N'-Bis[2,3-bis(acetyloxy)-1-propyl]-5-(3-bromohexahydro-2-oxo-1H-azepin-1-yl)-2,4,6-triiodo-1,3-benzenedicarboxamide To a solution of the title B compound (5.10 g, 4.50 mmol) in N,N'-dimethylacetamide (60 mL) was added finely powdered potassium carbonate (3.42 g, 24.8 mmol). The reaction mixture was stirred at room temperature for 21 hours. The solid particles were removed by filtration and the filtrate was concentrated in vacuo at 45° to give a pale yellow solid. The product was redissolved in ethyl acetate (250 mL) and washed with water (4×75 mL) and saturated aqueous sodium chloride (1×75 mL). The organic layer was dried over magnesium sulfate, filtered and concentrated to a light yellow solid (4.6 g). This material was purified by flash column chromatography over silica gel (elutant 75% ethyl acetate/hexane) to give pure N,N'-bis[2,3-bis(acetyl-oxy)-1-propyl]-5-(3-bromo-hexahydro-2-oxo-1H-azepin1-yl)-2,4,6-triiodo-1,3-benzenedicarboxamide as a white amorphous solid (3.4 g). TLC: Rf 0.21 (silica gel plate, ethyl acetate/ hexane 75:15 UV detection).

Microanalysis calc'd for $C_{28}H_{33}N_3BrI_3O_{11}$.0.20 $H_2O$: C, 31.98; H, 3.20; N, 4.00; Br, 7.60; I, 36.20; O, 17.03; Found: C, 32.35; H, 3.12; N, 3.87; Br, 7.60; I, 36.19; $H_2O$, 0.34.

D. 5-[3-(Acetyloxy)-hexahydro-2-oxo-1H-azepin-1-yl]-N,N'-bis[2,3-bis(acetyloxy)-1-propyl]-2,4,6-triiodo-1,3-benzenedicarboxamide To a stirred solution of the title C compound (3.30 g, 3.10 mmol) in glacial acetic acid (30 mL) were added silver acetate (2.59 g, 15.5 mmol) and acetic anhydride (0.32 g, 3.10 mmol). The mixture was heated to reflux for 135 hours. The excess silver acetate and the liberated silver bromide were filtered off and the filtrate was concentrated in vacuo at 45°. The resulting residue was dissolved in ethyl acetate (250 mL) and washed successively with water (2×60 mL), saturated aqueous sodium bicarbonate (2×60 mL), water (2×60 mL) and saturated aqueous sodium chloride (100 mL). the organic layer was dired over anhydrous magnesium sulfate, filtered and evaporated to an off-white solid. This crude material was purified by flash column chromatography over silica gel eluting with a stepwise gradient beginning from 70% ethyl acetate/hexane to 100% ethyl acetate increasing by 10% ethyl acetate after approximately 4 column volumes. Fractions containing pure title B pentaacetate were combined and concentrated in vacuo to give 2.04 g of an amorphous white solid. TLC: Rf 0.30 (silica gel plate, ethyl acetate/hexane 85:15,UV detection).

Microanalysis calc'd for $C_{30}H_{36}N_3I_3O_{13}$. 0.26$H_2O$: C, 34.91; H, 3.57; N, 4.07; I, 36.89; O, 20.56; Found: C, 34.94; H, 3.49; N, 3.76; I, 36.48; $H_2O$, 0.46

E. N,N'-Bis(2,3-dihydroxy-1-propyl)-5-(hexahydro-3-hydroxy-2-oxo-1H-azepin-1-yl)-2,4,6-triiodo-1,3-benzenedicarboxamide To a cold solution (5°) of the title D compound (2.00 g, 1.95 mmol) in anhydrous methanol (10 mL) was added a solution of sodium methoxide (0.2 mL) (prepared by reacting 0.52 mmol Na with 1 mL methanol). The reaction mixture was brought to room temperature and the stirring was continued for three hours. Upon completion, the reaction mixture was adjusted to pH 7 by slow addition of Dowex-50 (H$^+$) AG 50W-X8 cation exchange resin. The resin was removed by filtration and the filtrate was concentrated in vacuo. The resulting pale yellow solid was dissolved in hot water (50 mL), treated with activated carbon (100 mg) for 10 minutes, and then purified by low pressure reversed phase column chromatography on CHP-20 resin using ethanol-water (0–12%). Those fractions which contained the product were combined and evaporated in vacuo at 55° to obtain the title compound as a white solid. This material was dried under high vacuum at 55° to a constant weight. TLC: Rf 0.42 (silica gel plate, chloroform-methanol (7:3), UV detection).

Microanalysis calc'd for $C_{20}H_{26}N_3I_3O_8$.0.96 $H_2O$: C, 28.78; H, 3.37; N, 5.04; I, 45.62; O, 17.19; Found: C, 28.93; H, 3.12; N, 4.89; I, 45.48; $H_2O$, 2.08;

EXAMPLE 16

N-[[1,3,4-Trihydroxy-2-butyl]-5-[3-hydroxy-2-oxo-1-piperidinyl]-2,4,6-triiodo-1,3-benzenedicarboxamide A. 2-Tetrahydrofuroyl Chloride 2-Tetrahydrofuroic acid (413.5 mL, 500.0 g) was added to dimethylformamide (1.5 mL) and this was cooled to 15° C. under N$_2$. After purging the reaction vessel with nitrogen for 15 minutes, oxalyl chloride (469.5 mL, 683.1 g) was added dropwise to maintain the temperature at less than 25° C. This required from 3.75 to 5 hours. The crude product was distilled at 65° C. with a vacuum of 2 mm. The reaction mixture was distilled over 40 minutes. An average yield of 548.3 g of the title A product was isolated.

B. N-[3,5-Bis(chlorocarbonyl)-2,4,6-triiodophenyl]tetrahydro-2-furancarboxamide

N-[3,5-Bis(chlorocarbonyl)-2,4,6-triiodophenyl]amine (230.3 g, 386.6 mmoles) was charged to a flask blanketed with nitrogen. Tetrahydrofuran (276 mL, KF≦0.03%) was added to the flask and the mixture was agitated at 20° to 25° C. to dissolve the amine. The title A compound (104.0 g, 773.2 mmoles) was added in one portion to the flask. The solution was heated at reflux (65° to 70° C.) under nitrogen for ca. 6 hours until complete. Heptane (552 mL) was added in one portion and the mixture was heated at reflux (ca. 75°–80° C.) for 30 minutes. The suspension was then cooled to 0° to 10° C. over one hour and held at 0° to 10° C. for another hour. The product was isolated by vacuum filtration and washed with 3×350-mL portions of cold (0° to 10° C.) ethyl acetate. Drying the cake at 45° to 50° C. for 10 hours in vacuo (50 mm Hg) afforded 242.3 g of the product.

An 80 g portion of this material was suspended in tetrahydrofuran (640 mL), heated to obtain dissolution, and then filtered. Heptane (1280 mL) was added, the suspension was heated at reflux (75° to 78° C.) for 30 minutes, and then cooled to 0° to 10° C. over 90 minutes. After holding the slurry at 0° to 10° C. for another hour, the crystalline product was isolated by vacuum filtration and washed with 3×100 mL portions of cold (0° to 10° C.) ethyl acetate. Drying the cake at 45° to 50° C. for 10 hours in vacuo (50 mm Hg) afforded 71.5 g of high quality title B product (HPLC HI 100).

C. 2-(Acetyloxy)-N-[3,5-bis(chlorocarbonyl)-2,4,6-triiodophenyl]-5-bromopentanamide To a stirred solution of 100 g (0.144 moles) of title B compound in 1L of dry methylene chloride was added 6.80 mL (18.03 g, 0.072 moles) of boron tribromide (99.9%) at room temperature. The resulting slurry was stirred at room temperature. After stirring at room temperature for 2 hours, the reaction was only 92% complete so an additional 0.5 mL of boron tribromide was added. Stirring for another 1 hour resulted in complete conversion to the ring-opened bromo boronate. Then 8.5 mL (0.15 moles) of acetic acid was added followed by 27 mL (0.288 moles) of acetic anhydride and the resulting mixture stirred at reflux (40°–41° C.). The reaction mixture became homogeneous after stirring at reflux for 2 hours. After 4 hours, 500 mL of methylene chloride was removed via distillation, 500 mL of heptane was added and the reaction mixture cooled to room temperature. The resulting white precipitate was collected via filtration and washed with 500 mL of a solution of 50:50 methylene chloride:heptane that had been cooled to 5° C. The resulting white solid was dried under vacuum at 45° C. for 24 hours to yield 98.5 g of the title C product as a white solid, m.p. 194°–195° C.

49

Analysis calc'd for $C_{15}H_{11}NBrCl_2I_3O_5$: C, 22.06; H, 1.36; N, 1.71; total halogen, 65.07; Found: C, 22.17; H, 1.53; N, 2.04; total halogen, 65.71.

D. 2,4,6-Triiodo-5-(3-acetyloxy-2-oxo-1-piperidinyl)-1,3-benzenedicarboxylic acid bis-chloride The title C compound (48.96 g, 60 mM) was dissolved in 100 mL of N,N-dimethylacetamide and the solution was stirred under a positive pressure of nitrogen at 15° C. To this stirred solution diisopropylamine, 7.29 g (72 mM, 10.09 ml) was added in one lot using a syringe under nitrogen. After 30–35 minutes of stirring an off-white solid started to separate out and the solution became thicker. After 3 hours, the reaction mixture was quenched into cold water (5°–7° C., 1.5 Lt) containing 12 mL of 1N hydrochloric acid. 10–15 mL of fresh dimethylacetamide was used to rinse the reaction flask. The precipitated solids were filtered under suction, the wet cake suspended in 1.5 Lt of deionized water, stirred for two to three minutes and filtered. The suction dried solids weighed 91.9 g. The material was dried under vacuum at 40°–45° C. overnight yielding 42.4 g of the crude title D copounds as an almost colorless crystalline material.

This procedure was repeated to provide an additional 43.0 g of product.

81.29 g of the dried material from the two experiments was combined together and dissolved in 120 mL of dimethylacetamide and filtered under suction. The clear solution was transferred to a three necked round bottomed flask and an additional 20 mL of dimethylacetamide was used for rinsing the filter flask. The solution was stirred and treated with tetrahydrofuran (140 mL) followed by water (125 mL) to a cloud point. The addition of water increased the temperature from 22° to 26° C. The temperature was reduced to 20° C. and kept at 20° for 1 hour and 15 minutes. Thereafter the temperature was brought down to 10° C. and kept at temperature for 1 hour and 30 minutes. The crystalline solid was filtered and washed with 200 mL of 30% THF/water (V/V) to give 68.57 g of sandy white crystalline powder. This material was dried under vacuum at 40°–45° C. to yield 67.18 g of the title D compound.

E. (5-S-trans)-3-[3-(Acetyloxy)-2-oxo-1-piperidinyl]-5[[(6-hydroxy-2,2-dimethyl-1,3-dioxepan-5-yl)amino]-carbonyl]-2,4,6-triiodobenzoyl chloride To a solution of the title D compound (6.6 g, 9 mmol) in anhydrous dimethyacetamide (40 ml) was added triethyl amine (0.9 g, 9 mmol) and 4-amino-5-hydroxy-2,2-dimethyl-1,3-dioxepane (1.6, 9.9 mmol) and the mixture was stirred at room temperature for 16 hours. Dimethylacetamide was removed in vacuo and the residue was dissolved in ethyl acetate (150 ml), washed with water (100 ml), dried and solvent removal afforded the crude mono amide. The crude material was purified by column chromatography over silica gel (300 g) using hexane/ethyl acetate as the eluent to afford pure title E mono amide mono acid chloride (5.3 g) as a colorless glassy solid.

Elemental analysis calc'd for $C_{22}H_{24}N_2O_8I_3Cl$: C, 30.70, H, 2.81; N, 3.26; Cl, 4.12; I, 44.24; Found: C, 30.89; H, 2.73; N, 3.26; Cl, 4.08; I, 43.86.

F. N-[[1,3,4-Trihydroxy-2-butyl]-5-[3-hydroxy-2-oxo-1-piperidinyl]-2,4,6-triiodo-1,3-benzenedicarboxamide A solution of the title E compound (4.4 g, 5.1 mmol) in anhydrous dimethylacetamide (20 ml) was cooled and treated in a steel bomb with anhydrous ammonia (4 ml) at −78° C. The temperature of the reaction mixture was allowed to rise slowly to room temperature and the mixture was stirred for 18 hours. Ammonia was allowed to evaporate off and the resulting product without isolation was treated with 5M sodium hydroxide solution (2.0 ml) for 2 hours. At the end of 2 hours, the pH of the reaction mixture was adjusted to 0.5 with concentrated hydrochloric acid and the mixture was stirred for 16 hours. The solvents were removed in vacuo and the residue was dissolved in water (400 ml), the pH adjusted to 7 and the solution loaded on to a CHP-20P column (500 ml). The column was initially eluted with water to remove all the salts and then with water containing increasing amounts of ethanol. The product was eluted with 7–8% ethanol. Fractions containing the pure product were combined and solvent removal afforded pure title product as a colorless glassy solid (3.42 g, yield 88%).

Elemental analysis calc'd for $C_{22}H_{24}N_2O_8I_3Cl$: C, 26.90, H, 2.66; N, 5.54; I, 50.15; Found: C, 26.96; H, 2.81; N, 5.38; I, 50.54.

EXAMPLE 17

(Alternate synthesis for Example 8)

N,N'-bis(2,3-Dihydroxypropyl)-5-(3-hydroxy-2-oxo-1-piperidinyl)-2,4,6-triiodo-1,3-benzenedicarboxamide A. N,N'-bis(2,3-Dihydroxypropyl)-5-(3-acetyloxy-2-oxo-1-piperidinyl)-2,4,6-triiodo-1,3-benzenedicarboxamide To 50 g of the title D compound of Example 16 was added 544 mL of acetonitrile and 21.8 mL of triethylamine. A good agitation was maintained all through the reaction. (±)3-Amino-1,2-propanediol (APD), 14.24 g, dissolved in 68 mL of deionized water was then added within 10 minutes. Another 68 mL of deionized water was used to rinse the flask in which the APD solution was made and the addition funnel. The rinsings were also added to the reaction mixture. An endotherm of 7°–10° C. was observed. After the additions were complete, the reaction mixture was maintained at 25°–28° C. The reaction mixture which was initially a suspension became a clear solution after about 2 to 3 hours from the commencement of the addition of APD. Progress of the reaction was monitored by an in-process HPLC assay. As the reaction progressed, the bis coupled product maximized in about 10 hours. At the end of this time, the reaction flask was equipped for vacuum distillation and the solvent was removed under reduced pressure (approximately 30 inches of mercury) to obtain a final volume of 160 mL of a pale yellow colored solution (pH=8.65). This solution was used in the next step for purification on ion-exchange resins.

The so-prepared reaction mixture was allowed to drip on a resin bed and the elution rate was maintained at 25–30 mL/min. After the solution had been passed through the resin, the separatory funnel was charged with deionized water and elution was continued. Seventeen fractions, 250 mL each in volume, were collected. After assaying all the fractions by HPLC, fractions 1–8 were combined to obtain a total volume of 1750 mL (pH=4.4). This solution containing the title A product was used in the hydrolysis step.

B. N,N'-bis(2,3-Dihydroxypropyl)-5-(3-hydroxy-2-oxo-1-piperidinyl)-2,4,6-triiodo-1,3-benzenedicarboxamide To the solution containing the title A compound (1750 mL) obtained in the previous step was added 86 mL of IRA 900C (OH-) resin (1.7 equiv) and the suspension was agitated at 50°–55° C. Progress of the hydrolysis was monitored by an in-process HPLC assay. After about 5 hours, 29 mL more of the resin was added and the reaction was continued for an additional 2 hours. At the end of this time, the solution was brought to room temperature and filtered on a medium porosity sintered glass funnel. After disconnecting the vacuum, approximately 200 mL of deionized water was passed through the resin under gravity. The original filtrate and the water wash were combined to obtain a total volume of 2160 mL.

2-Butanol (230 mL) was heated and maintained at 38°–40° C. The solution from above was concentrated to dryness on a rotary evaporator keeping the bath temperature at 45°–50° C. to obtain 47.5 g of a solid. Of this, 43.4 g was dissolved in 76.5 mL of methanol and filtered. The clear filtrate was transferred to the addition funnel and added dropwise over a period of 25–30 minutes to the 2-butanol. An immediate precipitation of product took place. After the addition, the slurry was stirred for an additional hour at the same temperature and then cooled to 0° C. for 30 minutes. The resulting solid was then filtered and dried in a vacuum oven at 46° C. for 16 hours to obtain 38.3 g of crude solid.

A 1-L three necked flask fitted with a mechanical stirrer and an addition funnel was charged with 375 mL of acetone. The above solid material (37.5 g), dissolved in 75 mL of methanol, was transferred to an addition funnel and then added dropwise to 375 mL of acetone kept at 40° C. over a period of 20 minutes. An immediate prcipitation of product took place. After the addition, the slurry was cooled to 0° C. over a period of 30 minutes and held at the same temperature for an additional 30 minutes. The solid obtained was filtered, washed with 25 mL of acetone and dried in a vacuum over at 45° C. for 16 hours to obtain 32.7 g of a white solid. The material isolated and 21 g was dissolved in 100 mL of deionized water and the solution obtained ws concentrated to dryness under reduced pressure (20 mm of Hg) keeping the bath temperature at approximately 45° C. Final drying of the material was achieved in a vacuum over at 60° C. for 16 hours to obtain 18 g of the title B product as a glassy solid.

EXAMPLE 18

(Alternate synthesis for compound of Example 8)

N,N'-Bis(2,3-Dihydroxypropyl)-5-(3-hydroxy-2-one-1-piperidinyl)-2,4,6-triiodo-1,3-benzenedicarboxamide A. Tetrahydrofuroyl chloride Oxalyl chloride (63.5 g, 500 mmol) was added dropwise to tetrahydrofuroic acid 923.2 g, 200 mmol) at 0°. The solution was then stirred overnight at room temperature. Removal of excess oxalyl chloride (60°, 20 mm Hg), followed by distillation of the residue provided the desired tetrahydrofuroyl chloride as a colorless liquid (23.8 g), b.p. 88°–92° at 20 mm Hg.

B. Benzyl tetrahydrofuroate

Tetrahydrofuroyl chloride (15.0 g, 112 mmol) was added dropwise to a cold solution of benzyl alcohol (10.9 g, 101 mmol) and pyridine (20.0 g, 253 mmol) in Et$_2$O (200 mL). The solution was stirred at 0° for 40 minutes, then filtered to remove the side product pyridine hydrochloride. The filtrate was washed with 0.1 M HCl (50 mL), saturated aqueous NaHCO$_3$ (50 mL), and brine (50 mL), and then dried over MgSO$_4$. Filtration and evaporation of the solvent gave a yellow oil, which was distilled. Benzyl tetrahydrofuroate was obtained as a colorless oil (21.1 g) , b.p. 118° to 120° at 0.5 mm Hg.

Microanalysis calc'd for C$_{12}$H$_{14}$O$_3$ (206.2): C, 69.89; H, 6.84; O, 23.27; Found: C, 69.62; H, 6.89.

C. Benzyl 2-acetyloxy-5-chloro-pentanoate

To a suspension of freshly fused ZnCl$_2$ (35 mg, 0.25 mmol) in acetyl chloride (31 mL, 436 mmol) ws added dropwise benzyl tetrahydrofuroate (15 g, 72 mmol). The mixture was heated at reflux for 17 hours, by which time it turned black. Excess CH$_3$COCl was evaporated and the residue dissolved in Et$_2$O (200 mL). This solution was washed twice with saturated aqueous NaHCO$_3$ (50 mL). The organic layer was dried over MgSO$_4$, filtered and evaporated. The black residue was chromatographed over silica gel, eluting with 20:80 EtOAc-heptane. Fractions containing the desired ester were combined and evaporated to give a yellow oil. This oil was distilled to give the title C compound as a faintly yellow oil, which crystallized after several days in the refrigerator (17.6 g), b.p. 144 to 152° at 0.1 mm Hg, m.p. 40° to 41°.

Microanalysis calc'd for C$_{14}$H$_{17}$O$_4$Cl (284.7): C, 59.06; H, 6.02; Cl, 12.45; O, 22.48; Found: C, 59.22; H, 6.04; Cl, 12.63:

D. 2-Acetyloxy-5-chloro-pentanoic acid

5% Palladium on carbon (0.96 g) was suspended in a solution of the title C compound (15.3 g, 53.7 mmol) in ethyl acetate (170 mL) and HOAc (9.0 mL). The solution was shaken under an atmosphere of hydrogen (10 psi) for 1 hour, then filtered through a bed of celite. The solvent was evaporated and the residual oil was distilled to give the title D compound as a colorless oil (9.1 g), b.p. 135° to 136° at 0.03 mm Hg.

Microanalysis calc'd for C$_7$H$_{11}$O$_4$Cl (194.6): C, 43.20; H, 5.70; Cl, 18.22; O, 32.88; Found: C, 42.95; H, 5.80; Cl, 17.84.

E. 2-Acetyloxy-5-chloro-pentanoyl chloride

Oxallyl chloride (13.1 g, 103 mmol) was added to the title D compound (7.99 g, 41.1 mmol) and stirred at 25° overnight. Distillation gave unreacted oxallyl chloride followed by the title E compound (8.51 g) , b.p. 76°–78° at 0.5 mm Hg).

F. N,N-Bis[2,3-bis(acetyloxy)propyl]-5-[(2-acetyloxy-5-chloro-1-oxopentyl)-amino]-2,4,6-triiodo-1,3-benzenedicarboxamide The title E compound (2.77 g, 13.0 mmol) was added dropwise to a cold solution of N,N'-bis[2,3-bis(acetyloxy)propyl]-5-amino-2,4,6-triiodo-1,3-benzenedicarboxamide (prepared as described in Example 8-C) (8.73 g, 10.0 mmol) in dry DMA (400 mL). The solution was stirred at 25° overnight again. The reaction mixture ws purged with N$_2$ for 30 minutes to remove as much HCl as possible, then dissolved in EtOAc (200 mL) and washed with H$_2$O (100 mL), cold saturated aqueous NaHCO$_3$ (50 mL), and brine (50 mL). The organic layer was dried over MgSO$_4$, filtered, and evapoated to obtain a yellow foamy solid. This solid was chromatogrpahed over silica gel and eluted with 70:30 EtOAc-heptane. Fractions containing the product were combined and evapoated to give the title F compound as a white foamy solid (8.31 g). TLC: Rf 0.48 on silica gel, EtOAc, UV.

G. N,N-Bis [2,3-bis(acetyloxy)propyl]-5-(3-acetyloxy-2-oxo-1-piperdinyl)-2,4,6-triiodo-1,3-benzenedicarboxamide Powdered K$_2$CO$_3$ (3.32 g, 24 mmol) was added to a solution of the title F compound (6.00 g, 57.1 mmol) in DMA (29 mL) and stirred at 25° overnight. The reaction mixture was filtered and evaporated. The residual yellow oil was dissolved in ethyl acetate (100 mL) and washed with H$_2$O (50 mL) and brine (50 mL). The organic layer was dried over MgSO$_4$, filtered, and evaporated to give a white foamy solid. This solid was chromatographed over silica gel and eluted with 80:20 ethyl acetate-heptane. Fractions containing the pure product were combined and evaporated to give the title G compound as a white foamy solid (4.56 g)

H. N,N'-Bis(2,3-Dihydroxypropyl)-5-(3-hydroxy-2-one-1-piperidyl)-2,4,6-triiodo-1,3-benzenedicarboxamide To a solution of the title G compound (25 mg, 0.026 mmol) in anhydrous methanol (3 mL) was added a solution of sodium methoxide in methanol (0.2 mL/0.5 M solution), and the mixture stirred for 2 hours. The solution was neutralized by addition of AG 50 W-X-8 (H$^+$) resin which was filtered off and the filtrate concentrated to give 17 mg of the title product.

EXAMPLE 19

(Alternate Synthesis for Example 8-C)

5-[3-(Acetyloxy)-2-oxo-1-piperdinyl]-N,N-bis[2,3-bis(acetyloxy)propyl]-2,4,6-triiodo-1,3-benzenedicarboxamide A. N,N'-Bis[2,3-bis(acetyloxy)propyl]-2,4,6-triiodo-5-[[(tetrahydro-2-furanyl)carbonyl]amino]-1,3-benzenedicarboxamide To a stirred solution of N,N'-bis[2,3-bis(acetyloxy)propyl]-5-amino-2,4,6-triiodo-1,3-benzenedicarboxamide (8.73 g, 10 mmol) in N,N-dimethylacetamide (30 mL), was added in drops tetrahydro-2-furancarbonyl chloride (1.8 g, 13 mmol) (prepared as in part A of Example 18) at 0°–5°. After the addition, the mixture was stirred at 0°–5° for 0.5 hour, then at room temperature for 20 hours. Nitrogen gas was purged through the solution for 0.25 hour, and the N,N-dimethylacetamide was removed in vacuo at 40°. The residue was dissolved in ethyl acetate (200 mL), and the solution was washed successively with cold aqueous sodium bicarbonate (2×50 mL), water (2×50 mL) and saturated sodium chloride (2×50 mL). After drying over sodium sulfate, the solvent was removed in vacuo to obtain the title B furanilide as an off-white foamy material (9.27 g, crude). The crude product (7.2 g), upon purification by column chromatography over silica gel
(mobile phase: hexane/ethyl acetate) furnished N,N'-bis [2,3-bis(acetyloxy)propyl]-2,4,6-triiodo-5-[[(tetrahydro-2-furanyl)carbonyl]amino]-1,3-benzenedicarboxamide (6.19 g), m.p. 101°–104°.

Elemental analysis calc'd for $C_{27}H_{32}I_3N_3O_{12}$ (971.28): C, 33.39; H, 3.32; I, 39.20; N, 4.33; O, 19.77; Found: C, 33.39; H, 3.27; I, 38.78; N, 4.26.

B. 5-[3-(Acetyloxy)-2-oxo-1-piperdinyl]-N,N-bis[2,3-bis(acetyloxy)propyl]-2,4,6-triiodo-1,3-benzenedicarboxamide To a stirred solution of the title A furanilide (194 mg, 0.2 mmol) in dry ethyl acetate (5 mL) was added the HBr-Ac$_2$O reagent (3 mL, prepared by passing HBr gas through acetic anhydride at 0°–5° for 2 hours) at 0°–5°. The mixture was stirred at 5° for 2 hours, and then at room temperature for 75 hours. Nitrogen gas was purged through the reaction mixture for 15 minutes, and the solvent was evaporated in vacuo at 40°. The residue was dissolved in ethyl acetate (50 mL), and the solution washed successively with water, cold aqueous saturated NaHCO$_3$, water and brine. After drying over Na$_2$SO$_4$, the solvent was removed in vacuo to obtain the alpha-acetyloxy-omega-bromopentanoylanilide as a brownish semi-solid (220 mg). This material was immediately subjected to intramolecular cyclization by stirring with powdered potassium carbonate (0.3 g) in N,N-dimethylacetamide (5 mL) overnight. The mixture was filtered, and the solid material washed with ethyl acetate (20 mL). The filtrate was concentrated in vacuo to yield a brownish semi-solid, which, upon purification by silica gel chromatography using hexane/ethyl acetate, furnished the desired penta-acetate (99 mg) as a white amorphous solid.

The corresponding piperidinyl products were prepared using the methodology in the previous Examples.

EXAMPLE 20

(Alternate synthesis for Example 8-C)

5-[3-(Acetyloxy)-2-oxo-1-piperdinyl]-N,N-bis[2,3-bis(acetyloxy)propyl]-2,4,6-triiodo-1,3-benzenedicarboxamide To a stirred solution of the title A furanilide of Example 19 (194 mg, 0.2 mmol) in dry ethyl acetate (5 mL) was added freshly fused and powdered ZnCl$_2$ (6 mg). The mixture was placed in a preheated oil-bath (80°–85°) and stirred for 5 minutes when a homogeneous solution was obtained. To this was added acetyl chloride (0.4 mL) dropwise, and the mixture stirred at 80°–85° for 12 hours. The solvents were removed in vacuo, and the residue partitioned between ethyl acetate (50 mL) and water (10 mL). The organic layer was washed with water, dried over Na$_2$SO$_4$, and the solvent removed in vacuo to yield the alpha-acetyloxy-omega-chloro-pentanoylanilide as a dark gummy residue (210 mg). This was dissolved in N,N-dimethylacetamide (5 mL), treated with powdered potassium carbonate (0.2 g) and the mixture stirred overnight. The solid material was filtered off, and the filtrate concentrated in vacuo to give a brownish gummy product. Purification of this material by preparative TLC (CHCl$_3$/MeOH 9:1) furnished the pentaacetate as a white amorphous solid (61 mg).

The corresponding piperidinyl products were prepared using the methodology in the previous Examples.

EXAMPLE 21

(Alternate synthesis for Example 8-C)

N,N'-Bis[2,3-bis(acetyloxy)propyl]-5-(3-hydroxy-2-oxo-1-piperidinyl)-2,4,6-triiodo-1,3-benzenedicarboxamide To a stirred solution of N,N'-bis[2,3-bis(acetyloxy)propyl]-2,4,6-triiodo-5-[[(tetrahydro-2-furanyl)carbonyl] amino]-1,3-benzenedicarboxamide (0.25 g, 0.26 mmol) (the title compound of Example 19) in dry CH$_2$Cl$_2$ (5 mL) was added triethyl amine (0.01 mL). The solution was cooled to 0°–5°, and to this was added dropwise a solution of dimethylboron bromide in CH$_2$Cl$_2$ (0.12 g, 0.5 mL/2 mMol solution in CH$_2$CL$_2$). After stirring the mixture at 0°–5° for 6–8 hours, the mixture was added to a vigorously stirred solution of aqueous saturated sodium bicarbonate (5 mL). After stirring for 5 minutes, ethyl acetate (50 mL) and water (10 mL) were added. The organic layer was separated, washed with water, dried over anhydrous sodium sulfate, and concentrated in vacuo to yield the omega-bromo-alpha-hydroxypentanoyl anilide as an off-white fluffy solid (260 mg).

The material was immediately subjected to intramolecular cyclization by stirring a mixture of the anilide (260 mg) and powdered potassium carbonate (250 mg) in N,N-dimethylacetamide (5 mL) for 15 hours. The mixture was filtered, and the cake washed with ethyl acetate. The combined filtrate was concentrated in vacuo to yield a brownish solid (230 mg), which upon purification by silica gel chromatography (hexane/ethyl acetate) furnished pure N,N'-bis[2,3-bis(acetyloxy)propyl]-5-(3-hydroxy-2-oxo-1-piperidinyl)-2,4,6-triiodo-1,3-benzenedicarboxamide as a white fluffy solid (134 mg).

Elemental analysis calc'd for $C_{27}H_{32}I_3N_3O_{12}$ (971.28)+ 0.78 $H_2O$: C, 32.92; H, 3.43; I, 28.64; N, 4.26; O, 20.75; Found: C, 33.24; H, 3.13; I, 38.34; N, 3.94; $H_2O$, 1.42.

The corresponding piperidinyl products were prepared using the methodology in the previous Examples.

What is claimed is:

1. Compounds of the formula

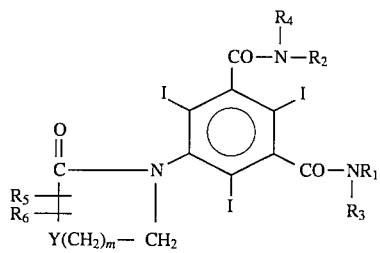

wherein $-Y(CH_2)_m-$ is $-CH_2-CH_2-$;

$R_1$, and $R_2$ are the same or different and are hydrogen, alkyl or hydroxyalkyl;

$R_3$ and $R_4$ are the same or different and are hydrogen, alkyl or $-CH_2CH_2OH$; $R_5$ is hydrogen, alkyl, $-CH_2CH_2OH$, $CH_2OH$ or OH and $R_6$ is alkyl, $-CH_2CH_2OH$, $CH_2OH$, OH or hydrogen and may be the same or different than $R_5$.

2. A compound according to claim 1, N,N'-Bis[2-hydroxy-1-(hydroxymethyl)ethyl]-5-[3-hydroxy-2-oxo-1-pyrrolidinyl]-2,4,6-triiodo-1,3-benzenedicarboxamide.

3. A compound according to claim 1, N,N'-Bis[2,3-dihydroxy-propyl]-5-[3-hydroxy-2-oxo-1-pyrrolidinyl]-2,4,6-triiodo-1,3-benzenedicarboxamide.

4. A compound according to claim 1, 5-[2-(Hydroxymethyl)-5-oxo-1-pyrrolidinyl]-N,N'-bis[2,3-dihydroxypropyl]-2,4,6-triiodo-1,3-benzenedicarboxamide.

5. A compound according to claim 1, N,N'-bis[2,3-dihydroxy-1-propyl]-5-[2-oxo-1-pyrrolidinyl]-2,4,6-triiodo-1,3-benzenedicarboxamide.

6. A compound according to claim 1, N,N'-bis[2-(hydroxy)-1-(hydroxymethyl)ethyl]-5-[2-(hydroxymethyl)]-5-oxo-1-pyrrolidinyl]-2,4,6-triiodo-1,3-benzenedicarboxamide.

* * * * *